US009567371B2

(12) United States Patent
Lapidot et al.

(10) Patent No.: US 9,567,371 B2
(45) Date of Patent: Feb. 14, 2017

(54) SHORT BETA-DEFENSIN-DERIVED PEPTIDES

(71) Applicant: Yeda Research and Development Co. Ltd., Rehovot (IL)

(72) Inventors: Tsvee Lapidot, Nes-Ziona (IL); Alexander Kalinkovich, Rehovot (IL); Matityahu Fridkin, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/880,238

(22) Filed: Oct. 11, 2015

(65) Prior Publication Data

US 2016/0122391 A1 May 5, 2016

Related U.S. Application Data

(62) Division of application No. 13/148,376, filed as application No. PCT/IL2010/000117 on Feb. 10, 2010, now Pat. No. 9,155,780.

(60) Provisional application No. 61/151,527, filed on Feb. 11, 2009.

(51) Int. Cl.
*C07K 7/52* (2006.01)
*A61K 38/12* (2006.01)
*A61K 38/17* (2006.01)
*C07K 14/47* (2006.01)
*A61K 38/00* (2006.01)

(52) U.S. Cl.
CPC .............. *C07K 7/52* (2013.01); *A61K 38/12* (2013.01); *A61K 38/1729* (2013.01); *C07K 14/4723* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,179,337 | A | 12/1979 | Davis et al. |
| 4,342,828 | A | 8/1982 | Takaku et al. |
| 5,665,863 | A | 9/1997 | Yeh |
| 6,365,583 | B1 | 4/2002 | MacFarland et al. |
| 7,291,631 | B2 | 11/2007 | Bridger et al. |
| 7,435,718 | B2 | 10/2008 | Tudan et al. |
| 2004/0209921 | A1 | 10/2004 | Bridger et al. |
| 2006/0275316 | A1* | 12/2006 | Weinberg ............... A61K 38/16 424/190.1 |
| 2010/0022750 | A1* | 1/2010 | Bishop ............. A61K 47/48246 530/345 |

FOREIGN PATENT DOCUMENTS

| | | |
|---|---|---|
| CA | 1297007 | 3/1992 |
| DE | 3027105 | 2/1981 |
| DE | 3723781 | 1/1988 |
| EP | 0169566 | 1/1986 |
| EP | 0215126 | 3/1987 |
| EP | 0217404 | 4/1987 |
| EP | 0220520 | 5/1987 |
| EP | 0230980 | 8/1987 |
| EP | 0231819 | 8/1987 |
| EP | 0237545 | 9/1987 |
| EP | 0243153 | 10/1987 |
| EP | 0263490 | 4/1988 |
| EP | 0272703 | 6/1988 |
| EP | 0331186 | 9/1989 |
| EP | 0335423 | 10/1989 |
| EP | 0344796 | 12/1989 |
| EP | 0355811 | 2/1990 |
| EP | 0370205 | 5/1990 |
| EP | 0373679 | 6/1990 |
| EP | 0396158 | 11/1990 |
| EP | 0401384 | 12/1990 |
| EP | 0456812 | 11/1991 |
| EP | 0459516 | 12/1991 |
| EP | 0459630 | 12/1991 |
| EP | 0459795 | 12/1991 |
| EP | 0473268 | 3/1992 |
| EP | 1541585 | 6/2005 |
| WO | WO 87/01132 | 2/1987 |
| WO | WO 91/07988 | 6/1991 |
| WO | WO 93/15211 | 8/1993 |
| WO | WO 01/85196 | 11/2001 |
| WO | WO 01/92309 | 12/2001 |
| WO | WO 0240512 | * 5/2002 |
| WO | WO 2007/074456 | 7/2007 |
| WO | WO 2007/126392 | 11/2007 |
| WO | WO 2008/075369 | 6/2008 |

(Continued)

OTHER PUBLICATIONS

International Preliminary Report on Patentability Dated Aug. 16, 2011 From the International Bureau of WIPO Re. Application No. PCT/IL2010/000117.
International Search Report and the Written Opinion Dated Aug. 19, 2010 From the International Searching Authority Re. Application No. PCT/IL2010/000117.
Notice of Allowance Dated Jun. 3, 2015 From the U.S. Appl. No. 13/148,376.
Office Action Dated May 20, 2013 From the Israel Patent Office Re. Application No. 214496.
Abraham et al. "Enhanced Unique Pattern of Hematopoietic Cell Mobilization Induced by the CXCR4 Antagonist 4F-Benzoyl-TN14003", Stem Cells, XP002629045, 25(9): 2158-2166, May 24, 2007.
Broxmeyer et al. "Rapid Mobilization of Murine and Human Hematopoietic Stem and Progenitor Cells With AMD3100, A CXCR4 Antagonist", The Journal of Experimental Medicine, XP009076434, 201(8): 1307-1318, Apr. 18, 2005.

(Continued)

*Primary Examiner* — Maury Audet

(57) ABSTRACT

The invention is directed to β-defensin-derived peptides and their use in modulating the activity of hematopoietic cells, particularly hematopoietic stem cells and progenitor cells. Specifically, the invention provides compositions and methods useful for promoting mobilization and transplantation of hematopoietic stem cells and progenitor cells. The invention further provides compositions and methods useful in the treatment of cancer.

8 Claims, 9 Drawing Sheets

(56) References Cited

FOREIGN PATENT DOCUMENTS

WO     WO 2009/140124     11/2009
WO     WO 2010/092571     8/2010

OTHER PUBLICATIONS

Burger et al. "CXCR4 Antagonists: Targeting the Microenvironment in Leukemia and Other Cancers", Leukemia, 23(1): 43-52, Jan. 2009.
Dar et al. "Mutual, Reciprocal SDF-1/CXCR4 Interactions Between Hematopoietic and Bone Marrow Stromal Cells Regulate Human Stem Cell Migration and Development in NOD/SCID Chimeric Mice", Experimental Hematology, 34(8): 967-975, Aug. 2006.
de Leeuw et al. "Structure-Dependent Functional Properties of Human Defensin 5", FEBS Letters, 581(3): 515-520, Feb. 6, 2007.
Devine et al. "Rapid Mobilization of Functional Donor Hematopoietic Cells Without G-CSF Using AMD3100, An Antagonist of the CXCR4/SDF-1 Interaction", Blood, 112(4): 990-998, Aug. 15, 2008.
Dhople et al. "The Human Beta-Defensin-3, An Antibacterial Peptide With Multiple Biological Functions", Biochimica et Biophysica Acta (BBA)—Biomembranes, 1758(9): 1499-1512, Sep. 2006.
Feng et al. "Cutting Edge: Human Beta Defensin 3—A Novel Antagonist of the HIV-1 Coreceptor CXCR4", The Journal of Immunology, 177(2):782-786, Jul. 15, 2006.
Funderburg et al. "Human Beta-Defensin-3 Activates Professional Antigen-Presenting Cells via Toll-like Receptors 1 and 2", PNAS, 104(47): 18631-18635, Nov. 20, 2007.
Gazitt et al. "Improved Mobilization of Peripheral Blood CD34+ Cells and Dendritic Cells by AMD3100 plus Granulocyte—Colony-Stimulating Factor in Non-Hodgkin's Lymphoma Patients", Stem Cells and Development, 16(4): 657-666, Sep. 4, 2007.
Goichberg et al. "cAMP-induced PKC Zeta Activation Increases Functional CXCR4 Expression on Human CD34+ Hematopoietic Progenitors", Blood, 107(3):870-879, Feb. 1, 2006.
Hendrix et al. "Safety, Pharmacokinetics, and Antiviral Activity of AMD3100, A Selective CXCR4 Receptor Inhibitor, in HIV-1 Infection", Journal of Aquired Immune Deficiency Syndromes, JAIDS, 37(2): 1253-1261, Oct. 1, 2004.
Hinrichsen et al. "Mouse Beta-Defensin-14, An Antimicrobial Ortholog of Human Beta-Defensin-3", Antimicrobial Agents and Chemotherapy, 52(5): 1876-1879, May 2008.
Hoover et al. "Antimicrobial Characterization of Human Beta-Defensin 3 Derivatives", Antimicrobial Agents and Chemotherapy, 47(9): 2804-2809, Sep. 2003.
Kalinkovich et al. "Functional CXCR4-Expressing Microparticles and SDF-1 Correlate with Circulating Acute Myelogenous Leukemia Cells", Cancer Research, 66(22): 11013-11020, Nov. 15, 2006.
Kalinkovich et al. "Small Human,—Defensin-3 Derived Peptide Induces Rapid and Preferential Mobilization of Mouse Hematopoietic Progenitor Cells Via SDF-1 Secretion", Hematologica—The Hematology Journal, 94: 296-296), 14th Congress of the European Hematology Association, Jun. 2009.
Kluver et al. "Structure—Activity Relation of Human β-Defensin 3: Influence of Disulfide Bonds and Cysteine Substitution on Antimicrobial Activity and Cytotoxicity", Biochemistry, 44 (28): 9804-9816, 2005.
Krishnakumari et al. "Antibacterial Activities of Synthetic Peptides Corresponding to the Carboxy-Terminal Region of Human β-Defensins 1-3", Peptides, 27(11): 2607-2613, Nov. 2006.
Lapidot et al. "Current Understanding of Stem Cell Mobilization: The Roles of Chemokines, Proteolytic Enzymes, Adhesion Molecules, Cytokines, and Stromal Cells", Experimental Hematology, 30: 973-981, 2002.
Liles et al. "Augmented Mobilization and Collection of CD34+ Hematopoietic Cells from Normal Human Volunteers Stimulated with Granulocyte—Colony-Stimulating Factor by Single-Dose Administration of AMD3100, a CXCR4 Antagonist† ", Transfusion, 45(3): 295-300, Mar. 2005.
Nishimura et al. "Effect of Defensin Peptides on Eukaryotic Cells: Primary Epithelial Cells, Fibroblasts and Squamous Cell Carcinoma Cell Lines", Journal of Dermatological Science, 36(2): 87-95, Nov. 2004.
Niyonsaba et al. "The Human Beta-Defensins (-1, -2, -3, -4) and Cathelicidin LL-37 Induce IL-18 Secretion Through P38 and ERK MAPK Activation in Primary Human Keratinocytes", The Journal of Immunology, 175(3): 1776-1784, 2005.
Roehrl et al. "Identification and Biological Characterization of Mouse β-Defensin 14, the Orthologue of Human β-Defensin 3", The Journal of Biological Chemistry, 283 (9): 5414-5419, Feb. 29, 2008.
Schneider et al. "Human defensins", Journal of Molecular Medicine, 83(8): 587-595, Aug. 2005.
Soruri et al. "Immunomodulation—β-Defensins Chemoattract Macrophages and Mast Cells But Not Lymphocytes and Dendritic Cells: CCR6 is Not Involved", European Journal of Immunology, 37(9): 2474-2486, Sep. 2007.
Spiegel et al. "Unique SDF-1—Induced Activation of Human Precursor-B ALL Cells as a Result of Altered CXCR4 Expression and Signaling", Blood, 103(8): 2900-2907, Apr. 15, 2004.
Tamamura et al. "Structure—Activity Relationship Studies on CXCR4 Antagonists Having Cyclic Pentapeptide Scaffolds", Organic & Biomolecular Chemistry, 3: 4392-4394, 2005.
Tavor et al. "CXCR4 Regulates Migration and Development of Human Acute Myelogenous Leukemia Stem Cells in Transplanted NOD/SCID Mice", Cancer Research, 64(8): 2817-2824, Apr. 15, 2004.
Tigue et al. "Granulocyte-Colony Stimulating Factor Administration to Healthy Individuals and Persons with Chronic Neutropenia or Cancer: An Overview of Safety Considerations from the Research on Adverse Drug Events and Reports Project", Bone Marrow Transplantation, 40(3): 185-192, 2007.
Vagima et al. "MT1-MMP and RECK Are Involved in Human CD34+ Progenitor Cell Retention, Egress, and Mobilization", The Journal of Clincal Investigation, XP002594412, 119(3): 492-503, Mar. 2009.
Varoga et al. "Human β-Defensin 3 Mediates Tissue Remodeling Processes in Articular Cartilage by Increasing Levels of Metalloproteinases and Reducing Levels of Their Endogenous Inhibitors", Arthritis & Rheumatism 52 (6): 1736-1745, Jun. 2005.
Wu et al. "Engineering Disulfide Bridges to Dissect Antimicrobial and Chemotactic Activities of Human β-Defensin 3", PNAS 100(15): 8880-8885, Jul. 22, 2003.
Zeng et al. "Targeting the Leukemia Microenvironment by CXCR4 Inhibition Overcomes Resistance to Kinase Inhibitors and Chemotherapy in AML", Blood, 113(24): 6215-6224, Jun. 11, 2009.

* cited by examiner

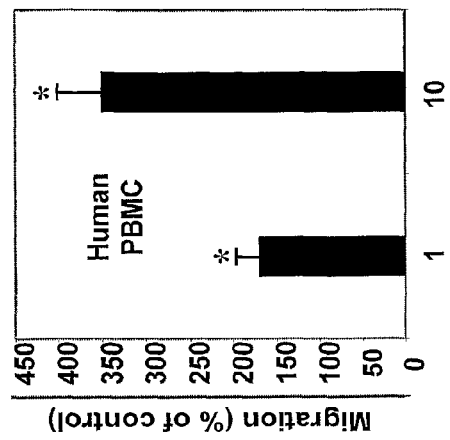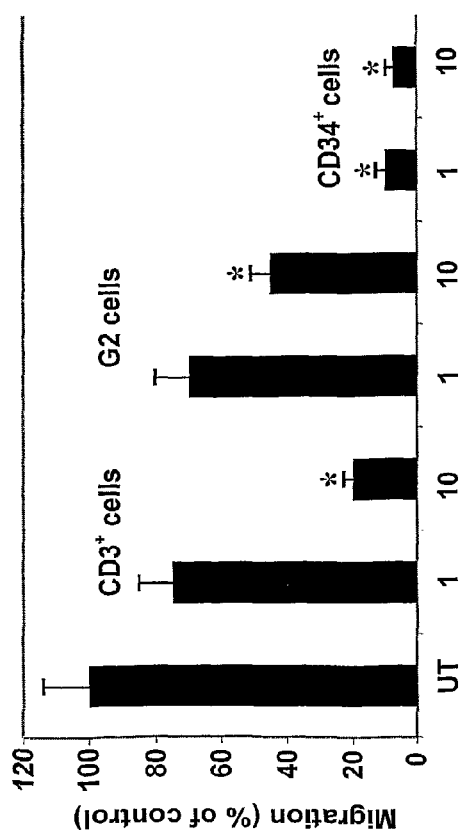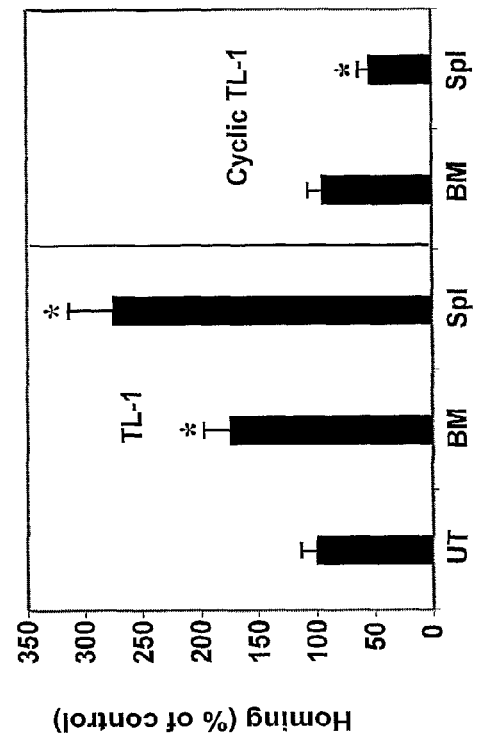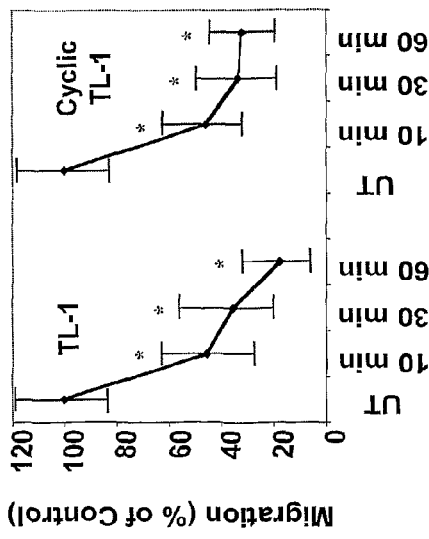

SHORT BETA-DEFENSIN-DERIVED PEPTIDES

RELATED APPLICATIONS

This application is a division of U.S. patent application Ser. No. 13/148,376 filed on Aug. 8, 2011, which is a National Phase of PCT Patent Application No. PCT/IL2010/000117 having international filing date of Feb. 10, 2010, which claims the benefit of priority of U.S. Provisional Patent Application No. 61/151,527 filed on Feb. 11, 2009. The contents of the above applications are all incorporated by reference as if fully set forth herein in their entirety.

FIELD OF THE INVENTION

The invention is directed to β-defensin-derived peptides and their use in modulating the activity of hematopoietic cells, including hematopoietic stem cells and progenitor cells.

BACKGROUND OF THE INVENTION

Transplantation of stem cells is a preferred strategy in the treatment of a variety of hematological malignancies and disorders. In recent years, the use of peripheral blood as a source of hematopoietic stem and progenitor cells (HSPC) for transplantation after a high-dose chemotherapy has emerged as a common clinical practice. Successful transplantation requires the infusion of a sufficient number of HSPC capable of homing and engraftment to the bone marrow (BM), and regenerating a full array of hematopoietic cell lineages. Under steady-state conditions, there are very low frequencies of circulating HPSC. However, these low levels can be amplified by a process termed HSPC mobilization. Thus, elevating the number of HSPC mobilized to the blood will improve the yield of cell collection for transplantation and will also have the potential to shorten recovery from cytopenia and reduce morbidity and mortality.

The cytokine granulocyte colony-stimulating factor (G-CSF) is so far the major mobilizing agent inducing a dramatic elevation in the number of HSPC in the blood (Lapidot, T. & Petit, I., 2002). However, G-CSF therapy is very expensive and requires a 5 day repeated dosing, and its efficacy in HSPC mobilization greatly varies among different patients. In addition, G-CSF therapy is frequently associated with side effects such as bone pain, headache and myalgia (Tigue, C. C., et al., 2007). Hence, improved methods to mobilize peripheral blood HSPC for hematopoietic rescue are warranted.

Evidence suggests that interactions between the chemokine stromal-derived factor-1 (SDF-1, also named CXCL12) and its major receptor CXCR4 play a crucial role in HPSC mobilization, homing, engraftment, survival and retention within the BM (Dar, A., Kollet, O. & Lapidot, T., 2006). Thus, disruption of SDF-1/CXCR4 interactions may result in mobilization of HSPC. Indeed, blocking of CXCR4 with its specific antagonist AMD3100 results in the rapid mobilization of CD34$^+$ hematopoietic progenitor cells (HPC) from the human BM to the blood (Broxmeyer, H. E., et al., 2005, Liles, W. C., et al., 2005, Dvine et al., 2008). In addition, combining AMD3100 with G-CSF has produced an additive effect (Gazitt, Y., Freytes, C. O., Akay, C., Badel, K. & Calandra, G., 2007). U.S. Pat. No. 6,365,583 further discloses a method to treat a subject who would be benefited by elevation of white blood cell count which method comprises administering to said subject a cyclic polyamine such as AMD3100. However, a clinical trial with AMD3100 in HIV-infected individuals was halted due to its cardio-toxic effect (Hendrix, C. W., et al., 2004).

A strong and rapid mobilization effect was demonstrated in the murine system by using another CXCR4 antagonist, 4F-benzoyl-TN14003, that provided also an additive effect with G-CSF (see, for example, Abraham, M., et al., 2007 and WO 2008/075369). Mobilization of human HSPC by 4F-benzoyl-TN14003 has not been clinically tested. Various other agents have been suggested to be involved in modulating CXCR4/SDF-1 interactions and are being evaluated for their therapeutic potential in affecting different functions and processes mediated by hematopoietic cells, including HSPC mobilization. For example, U.S. Pat. No. 7,435,718 is directed to SDF-1 analogs having CXCR4 antagonistic activity useful in the treatment of hematopoietic cells in vitro and in vivo, for example in increasing the rate of hematopoietic stem or progenitor cellular multiplication, self-renewal, expansion, proliferation, or peripheralization. WO 01/85196 suggests that hematopoietic cell proliferation may be modulated by ex vivo exposure to CXCR4 antagonists derived from SDF-1 (P2G), in which glycine is substituted for proline at amino acid position 2.

Other such agents are described, for example, in U.S. Pat. No. 7,291,631 and PCT Pub. No. WO 01/85196 and by Zeng et al. (2008), Tavor et al. (2004), Tamamura et al. (2005) and Burger and Peled (2009). U.S. Pat. Appl. Pub. No. 2004/0209921 discloses heterocyclic compounds that bind to chemokine receptors, including CXCR4 and CCR5, which may possess protective effects against infection of target cells by a human immunodeficiency virus (HIV). Other potential uses for these compounds suggested by '921 are enhancing the population of progenitor and/or stem cells, stimulating the production of white blood cells, and/or effecting regeneration of cardiac tissue.

Other publications relate to the use of CXCR4 antagonists in cancer therapy. For example, WO 2009140124 is directed to antibodies that bind human CXCR4 and are characterized as having high affinity and strong neutralizing properties, disclosed to be useful in the treatment of tumor growth, invasion, angiogenesis and metastasis.

PCT Pub. No. WO 2007/074456, to some of the inventors of the present invention, is directed to phenylalanine, cysteine, derivatives of said amino acids, peptides comprising them, and to their use in diseases, disorders or conditions whose pathology is caused by or associated with CXCR4 activity and/or cell motility, such as cancer, acquired immunodeficiency syndrome (AIDS), inflammation and metastasis.

It has been suggested that certain CXCR4 mediated activities may also be affected by a defensin peptide, namely human β-defensin-3 (HBD3). Defensins are the members of antimicrobial peptides (AMPs) family employed as an innate immunity nonspecific defensive mechanism. Shortly after microbial infection, the AMPs are released and rapidly mobilized to neutralize a broad range of microorganisms (de Leeuw, E. et al., 2007). Being highly positively charged and disulfide-bonded, defensins bind to negatively charged bacterial membrane targets including LPS, polysaccharides, teicholic acids and phopspolipids. Membrane depolarization and permeabilization appear to be the predominant mechanisms of action of antimicrobial defensins (Schneider, J. J. et al., 2005). The presence of phosphatidilcholines in cytoplasmic membranes of eukaryotic cells and its electrostatic effects may account, at least in part, for the selectivity of defensins to bacteria and the relatively lower toxicity to eukaryotic cells (Nishimura, M., et al., 2004). So far, however, intracellular processing, storage, and release pathways of the defensins remain to be defined.

HBD3 is a 45 amino acids cysteine-enriched and highly cationic peptide, characterized by an exceptionally high net charge (+11), a broad spectrum of antimicrobial activity and relatively low cytotoxicity. It is expressed by epithelial cells, monocytes, dendritic cells and keratinocytes, and its expression is induced by IL-1, TNF-α, IFN-γ as well as by growth factors and various bacteria and viruses, whereas corticosteroids and cysteine proteases Cathepsins B, L, and S degrade and inactivate HBD3 (Dhople, V., Krukemeyer, A. & Ramamoorthy, A., 2006).

Apart from the antibacterial activity, HBD3 has been reported to inhibit HIV entry to the CXCR4 expressing target cells, and to internalize CXCR4 and decrease SDF-1-induced chemotaxis of T cells (Feng, Z. et al., 2006). HBD3 also increases migration of monocytes and CCR6-transfected human embryonic kidney HEK-293 cells (Wu, Z., et al., 2003). By direct binding to CCR6, HBD3 induces secretion of the proinflammatory cytokine IL-18 in human keratinocytes (Niyonsaba, F. et al., 2005) although participation of CCR6 as a possible receptor for HBD3 is doubtful (Soruri, A. et al., 2007). In addition, HBD3 induces the secretion of tissue remodeling proteins such as matrix metalloproteinases (MMP-1 and MMP-13) and reduces the levels of MMPs' inhibitors (TIMP-1/-2) in human cartilage (Varoga, D., et al., 2005). More recently it has been shown that HBD3 can induce expression of the co-stimulatory molecules CD80, CD86, and CD40 on monocytes and myeloid dendritic cells in a toll-like receptor (TLR)-dependent manner (Funderburg, N., et al., 2007). PCT Pub. No. WO 01/92309 relates to HBD3 and antimicrobial compositions containing it and methods of using same.

Mouse β-defensin 14 (MBD14) is an ortholog of HBD3 having a 68% sequence homology and similar spectrum of antimicrobial activity (Hinrichsen, K., et al., 2008, Rohrl, J. et al. 2008). MBD14 has chemotactic activity for HEK-293 cells (Soruri, A. et al., 2007) but its effects on CXCR4/SDF-1 interactions have not been determined.

The ability of HBD3 to modulate certain CXCR4/SDF-1 dependent activities implies that it may potentially affect HPC mobilization. However, complicated and costly synthesis, limited stability, and unknown toxicology and pharmacokinetics impair its therapeutic use, particularly systemically. Thus, the clinical effects of HBD3 in the mammalian system, particularly in the context of leukocyte mobilization and other therapeutic uses, remain to be investigated.

Hoover et al. (2003) examined several peptides derived from different regions of HBD3, including 36-38 amino acid (aa) fragments corresponding to carboxy terminal (C') segments of HBD3, as well as shorter peptides in which the two cysteine residues were substituted for serine residues. Hoover et al. disclose that these peptides have anti-microbial properties, with different peptides having different target specificities.

Kluver et al. (2005) disclose certain other peptides and fragments of HBD3, including 27 and 40 aa C' fragments of HBD3. These peptides varied in their antimicrobial activity as well as in their cytotoxicity to human hematopoietic cells and hemolytic activity, wherein some of these C' fragments were highly toxic at 50 μM.

Krishnakumari et al. (2006) investigated the antibacterial activities of synthetic peptide analogs of human β-defensins, including a 22 aa peptide corresponding to the C' of HBD3, wherein two cysteines were deleted.

WO 2007/126392 relates to isolated antimicrobial peptides which are linear analogs of HBD3, or fragments thereof. WO '392 teaches that the wild type (45-aa) HBD3 contains three disulfide, bonds (between positions 11 and 40, positions 18 and 33 and positions 23 and 40, respectively) which define its three dimensional folding; in the claimed peptides, one or more of the cysteine residues of HBD3 has been replaced by other amino acids or derivatives thereof, or by protected cysteine residues or derivatives thereof, or have been deleted, thereby removing these structural constrains. According to this publication, the linear backbone structure of HBD3 derivatives is a key structural determinant to decrease cytotoxicity to mammalian cells. WO '392 discloses that the claimed peptides may be used for inhibiting and/or reducing the growth of microorganisms, e.g. as medicaments for topical administration, eye drop compositions, contact lens solutions or medical device coatings. Among the disclosed sequences is a linear peptide derived from the C-terminus of wild type HBD3, corresponding to SEQ ID NO: 1 of the present invention.

None of the art discloses or suggests cyclic HBD3-derived peptides in which the N-terminus and the C-terminus of the peptide are linked through a peptide bond, or the use of β-defensin peptides as anti-cancer agents. Nor does the art teach or suggest that short peptides derived from HBD3 may be used effectively and safely for promoting HPSC mobilization and engraftment. There remains an unmet medical need for developing additional agents and protocols for cancer therapy and for providing improved bone marrow transplantation and recovery.

SUMMARY OF THE INVENTION

The present invention is directed to β-defensin-derived peptides and their use in regulating the activity of hematopoietic cells and other CXCR4-expressing cells. Specifically, the invention provides short peptides derived from the C' of human β-defensin 3 (HBD3) and homologs thereof, useful for modulating mobilization and cell motility.

The invention is based, in part, on the surprising discovery, that TL-1, a linear 10 amino acid (aa) peptide derived from HBD3 (RGRKCCRRKK, SEQ ID NO: 1), and its homolog linear peptide AK-1 (SGRKCCRKKK, SEQ ID NO: 2), derived from mouse β-defensin 14 (MBD14), induce rapid and robust mobilization of hematopoietic progenitor cells (HPC) and white blood cells (WBC) in an in vivo mouse model, either alone or in combination with granulocyte colony-stimulating factor (G-CSF). The mobilizing activity was accompanied by a significant elevation in SDF-1 secretion and an increased activity of metalloproteinase-2 secreted by MS-5 stromal cells. TL-1 was also unexpectedly found to increase the homing of G2 cells to the bone marrow (BM) and spleen of NOD/SCID mice, demonstrating its ability to promote engraftment of hematopoietic cells in vivo.

While peptide cyclization has been associated in some cases with improved metabolic stability, the effects of cyclization on the structure and resulting activity of the peptide cannot be predicted. The inventors synthesized a cyclized derivative of TL-1, herein designated cTL-1 (((Cyclo)R-GRKCCRRKK, SEQ ID NO: 3), and examined its effects on CXCR4-dependent functions. Unexpectedly, it was discovered that, in contrast to its linear counterpart, cTL-1 did not induce mobilization of HPC or WBC. Rather, this derivative was surprisingly found to decrease the homing of G2 leukemic cells to the BM and spleen in the NOD/SCID mouse model, demonstrating its efficacy as an anti metastatic agent.

In addition, all tested peptides, namely TL-1, AK-1 and cTL-1, were found to be non-toxic to human cells, as opposed to previous reports on other β-defensin-derived peptides.

According to a first aspect of the invention, there is provided a novel HBD3-derived peptide analog, having unique structural properties formed and preserved by a peptide bond linking the N-terminus and the C-terminus of the peptide. These structural properties endow the peptide with unique and advantageous functional properties enabling its use in cancer therapy, as described in greater detail below.

Thus, certain embodiments of the invention are directed to a cyclic peptide of the sequence: 1,10-cyclo[RGRKCCR-RKK], (cTL-1, SEQ ID NO: 3), wherein the arginine at position 1 ($R_1$) is linked through a peptide bond to the lysine at position 10 ($K_{10}$). In another embodiment, the peptide is a cyclized homolog of cTL-1, having at least 70% sequence homology to SEQ ID NO: 3 and at least 70% identity with regard to the overall positive charge density of SEQ ID NO: 3, wherein the N-terminus and the C-terminus of the peptide are linked through a covalent bond (e.g. a peptide bond), and wherein the two adjacent cysteines at positions 5 and 6 of SEQ ID NO: 3 are retained.

In another aspect, there is provided a pharmaceutical composition containing an effective amount of a cyclic peptide as set forth in SEQ ID NO: 3 or a homolog thereof as defined herein, and one or more pharmaceutically accepted carriers, excipients or diluents.

In another aspect, the invention provides a method for reducing or inhibiting cancer metastasis in a subject in need thereof, comprising administering to the subject an effective amount of a cyclic peptide as set forth in SEQ ID NO: 3 or a homolog thereof as defined herein. In another embodiment, the subject is afflicted with a tumor characterized by CXCR4 expression of at least a portion of the tumor cells. In another embodiment, said tumor is of hematopoietic origin. In a particular embodiment, said tumor is leukemia.

In another aspect, the invention provides a method for reducing or inhibiting migration or homing of CXCR4-expressing malignant cells to the bone marrow of a subject in need thereof, comprising contacting the cells with an effective amount of a cyclic peptide as set forth in SEQ ID NO: 3 or a homolog thereof as defined herein. In one embodiment, the contacting is performed in vivo. In another embodiment, the contacting is performed ex vivo. In another embodiment, said malignant cells are of hematopoietic origin. In a particular embodiment, said malignant cells are leukemic cells.

According to certain other aspects of the present invention, there are provided novel compositions and methods for improved bone marrow transplantation.

Thus, certain embodiments of the invention are directed to an isolated peptide having an N-terminus (N') and a C-terminus (C'), wherein the peptide is selected from the group consisting of:
a. RGRKCCRRKK (TL-1, SEQ ID NO: 1);
b. SGRKCCRKKK (AK-1, SEQ ID NO: 2); and
c. a homolog of TL-1, having at least 70% sequence homology to SEQ ID NO: 1 and at least 70% identity with regard to the overall positive charge density of SEQ ID NO: 1, wherein the two adjacent cysteines at positions 5 and 6 of SEQ ID NO: 1 are retained, and wherein said homolog induces or enhances mobilization of hematopoietic progenitor and/or stem cells.

It is surprisingly demonstrated herein, that these peptides promote mobilization and engraftment, wherein co-administration of these peptides with Granulocyte Colony-Stimulating Factor (G-CSF) provides an additive effect. Accordingly, in another aspect, the invention provides a pharmaceutical composition containing an effective amount of a peptide selected from SEQ ID NOs: 1 and 2 and homologs thereof as defined herein, and one or more pharmaceutically accepted carriers, excipients or diluents, said composition further comprising at least one agent (e.g. cytokine) which stimulates mobilization of hematopoietic cells. In a particular embodiment, the agent comprises an effective amount of G-CSF.

In another aspect, the invention provides a method for elevating the levels of hematopoietic cells in peripheral blood of a subject comprising administering to the subject an effective amount of a peptide selected from SEQ ID NOs: 1 and 2 and homologs thereof as defined herein. In some embodiments, the method may be used to elevate the levels of hematopoietic progenitor and/or stem cells (HSPC) in peripheral blood, e.g. for mobilizing and subsequent harvesting HSPC for bone marrow transplantation. In certain embodiments, the peptide may be administered to said subject in combination with one or more agents used to induce mobilization of white blood cells, e.g. with at least one cytokine that stimulates mobilization of hematopoietic cells. In one preferable but optional embodiment, the peptides of the invention are administered in combination with G-CSF or an analog or derivative thereof. In another embodiment, the peptide is TL-1 (SEQ ID NO: 1). In another embodiment, the peptide is AK-1 (SEQ ID NO: 2).

In another aspect, the invention provides a method for obtaining a therapeutically effective amount of hematopoietic precursor cells from a subject, comprising:
a) administering to the subject a peptide selected from SEQ ID NOs: 1 and 2 and homologs thereof as defined herein in an amount sufficient to elevate the levels of hematopoietic precursor cells in peripheral blood of the subject;
b) harvesting said precursor cells (e.g. by apheresis); and optionally
c) repeating steps (a) and (b) until a therapeutically effective amount of hematopoietic precursor cells is obtained.

In one embodiment, the peptide is administered in combination with G-CSF. In another embodiment, the peptide is TL-1 (SEQ ID NO: 1). In another embodiment, the peptide is AK-1 (SEQ ID NO: 2).

In another aspect, there is provided a method for engrafting hematopoietic precursor cells in a patient in need of hematopoietic precursor cell transplantation, comprising the steps of:
a) administering to a donor subject a peptide selected from SEQ ID NOs: 1 and 2 and homologs thereof as defined herein in an amount sufficient to elevate the levels of hematopoietic precursor cells in peripheral blood of the subject;
b) harvesting hematopoietic precursor cells from peripheral blood of said subject (e.g. by apheresis);
c) optionally repeating steps (a) and (b) until a therapeutically effective amount of hematopoietic precursor cells is obtained; and
d) transplanting the resulting cells into a recipient patient in need thereof.

In one embodiment, the donor subject and the recipient patient are the same (i.e. when performing an autologous transplantation). In another embodiment, the donor subject and the recipient patient are not the same (i.e. when performing an allogeneic transplantation). Optionally, the method further comprises administering to the recipient patient a peptide selected from SEQ ID NOs: 1 and 2 and homologs thereof as defined herein, in an amount sufficient to enhance engraftment of said cells. In one embodiment, the peptide is administered in combination with G-CSF. In another embodiment, the peptide is TL-1 (SEQ ID NO: 1). In another embodiment, the peptide is AK-1 (SEQ ID NO: 2).

In another embodiment, the invention provides a method for enhancing engraftment of HSPC in a subject undergoing HSPC transplantation, comprising administering to said subject a peptide selected from SEQ ID NOs: 1 and 2 and homologs thereof as defined herein, in an amount sufficient to enhance engraftment of said cells.

In another aspect, there is provided a method of increasing G-CSF-induced hematopoietic precursor cell mobilization, comprising administering to a subject an effective amount of G-CSF in concurrent or sequential combination with a peptide selected from SEQ ID NOs: 1 and 2 and homologs thereof as defined herein. In another embodiment, the peptide is TL-1 (SEQ ID NO: 1). In another embodiment, the peptide is AK-1 (SEQ ID NO: 2).

In other embodiments, the peptides of the invention are used for mobilizing malignant hematopoietic cells from the bone marrow or other tissue sites, thus improving their accessibility to cancer therapy (e.g. to conventional chemotherapy protocols). Thus, in another aspect, there is provided a method of inducing mobilization of malignant hematopoietic cells, comprising administering to a subject an effective amount of a peptide selected from SEQ ID NOs: 1 and 2 and homologs thereof as defined herein. In another embodiment, the peptide is TL-1 (SEQ ID NO: 1). In another embodiment, the peptide is AK-1 (SEQ ID NO: 2).

In another aspect, there is provided a method for treating cancer in a subject in need thereof, comprising: 1) administering to the subject an effective amount of a peptide selected from SEQ ID NOs: 1 and 2 and homologs thereof as defined herein; and 2) administering to said subject an effective amount of a cancer therapy. In another embodiment, the cancer is of hematopoietic origin. In another embodiment, the cancer is characterized by CXCR4 expression of at least a portion of the cancer cells. In another embodiment, the peptide is TL-1 (SEQ ID NO: 1). In another embodiment, the peptide is AK-1 (SEQ ID NO: 2).

Other objects, features and advantages of the present invention will become clear from the following description and drawings.

BRIEF DESCRIPTION OF THE DRAWINGS

FIGS. 8A-8D. Effect of TL-1 and cyclic TL-1 on in vitro and in vivo cell migration. (A, C) Human CD3$^+$, G2, cord blood CD34$^+$ and peripheral blood mononuclear (PBMC) cells were preincubated with 1 and 10 μM TL-1 for 3 hrs in serum free medium, washed and allowed to migrate towards SDF-1. Migrated cells were collected and calculated by flow cytometry. Percentage of migrated cells is presented as compared to untreated (UT) control taken as 100%. (B) G2 cells were similarly preincubated with 10 μM TL-1 or cTL-1 for the indicated periods of time and percentage of migrated cells is depicted. (D) Homing assay. G2 cells were similarly preincubated with 10 μM TL-1 or cTL-1 for 3 hrs, washed and i.v. injected (10×10$^6$/mouse) to non-irradiated NOD/SCID mice. Percentage of G2 cells in the murine BM and spleens was determined by staining with anti-human CD45 Ab and compared with untreated (UT) cells. Data shown are the mean±SD of 2 separate experiments. *P<0.05 compared to control.

FIG. 10A—effect of TL-1 on CXCR4 expression. FIG. 10B—effect of cTL-1 on CXCR4 expression. FIG. 10C—effects of TL-1 and cTL-1 on CCR5 expression.

DETAILED DESCRIPTION OF THE INVENTION

Figure 1:
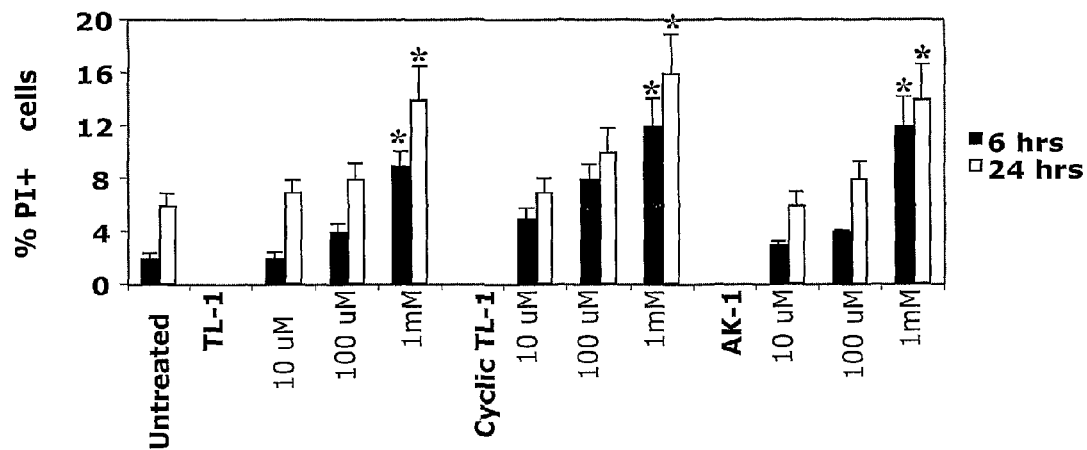
FIG. 1. Low cellular toxicity of TL-1, AK-1, and cyclic TL-1. G2 cells (1×10$^6$/ml) were cultured in 96-well flat-bottom wells in serum free IMDEM culture medium supplemented with L-glutamine and antibiotics, for 6 and 24 h at 37° C. with the indicated peptides. Untreated cells served as a control. After treatment, cells were stained with propidium iodide (PI) and its exclusion was analyzed by flow cytometry. Data shown are the percentage of Pr (dead) cells. Vertical bars represent standard deviation of duplicate experiments. *P<0.05 compared to untreated control.

The invention is directed to β-defensin-derived peptides and their use in modulating the activity of hematopoietic cells, particularly hematopoietic stem cells and progenitor cells. Specifically, the invention provides compositions and methods useful for promoting mobilization and transplantation of hematopoietic stem cells and progenitor cells. The invention further provides compositions and methods useful in the treatment of cancer.

Peptides

According to a first aspect of the present invention, there is provided a cyclic peptide of the sequence: Cyclo(R-GRKCCRRKK), (cTL-1, SEQ ID NO: 3), wherein the arginine at position 1 ($R_1$) is linked through a peptide bond to the lysine at position 10 ($K_{10}$). In another embodiment, the peptide is a cyclic homolog of SEQ ID NO: 3 having at least 70% sequence homology to SEQ ID NO: 3. In another embodiment, the peptide is a cyclic homolog of SEQ ID NO: 3 having at least 70% of the electric characteristics of SEQ ID NO: 3. In another embodiment, the two adjacent cysteines at positions 5 and 6 of SEQ ID NO: 3 are retained. In some embodiments, the peptide is a cyclized homolog of cTL-1, having at least 70% sequence homology to SEQ ID NO: 3 and at least 70% identity with regard to the overall positive charge density of SEQ ID NO: 3, wherein the N-terminus and the C-terminus of the peptide are linked through a covalent bond (e.g. a peptide bond and wherein the two adjacent cysteines at positions 5 and 6 of SEQ ID NO: 3 are retained. In another embodiment, the homolog reduces or inhibits migration or homing of CXCR4-expressing cells, e.g. reduces migration of CXCR4 expressing malignant cells induced by SDF-1.

As used herein, the terms "cyclic" or cyclized" denote a peptide or polypeptide whose amino and carboxy termini are themselves linked together with a covalent bond, including but not limited to a peptide bond, forming a continuous (e.g. circular) chain. In general, such compounds form covalently closed circles, and thus are not "loop structures", such as may be formed by formation of a disulfide bond between cysteines in a polypeptide having more than 3 or 4 residues. The term "cyclic peptide" as used herein refers to a preferable embodiment of the invention, wherein the peptide is composed of naturally-occurring amino acids that are covalently linked to one another by peptide bonds, where a peptide bond is —(C=O)—(N—H)—. In other embodiments, the invention relates to cyclized peptides, which encompass peptides rendered cyclic by a lactam bridge. Lactams can be of several types, such as "head-to-tail" (carboxy terminus to amino terminus), "head-to-side chain" (carboxy terminus respectively to a side chain amino or carboxyl group) and "side chain-to-side chain" (amino group of one side chain and carboxyl group of another side chain). In certain other embodiments, the cyclized peptides encompass peptides in which the two terminal amino acids are bonded together by a synthetic non-peptide bond such as a thioether, phosphodiester, disiloxane, azo or urethane bond. Every possibility represents a separate embodiment of the invention.

In another aspect, the invention relates to an isolated non-cyclized peptide, wherein the peptide is selected from the group consisting of:
  a. RGRKCCRRKK (TL-1, SEQ ID NO: 1);
  b. SGRKCCRKKK (AK-1, SEQ ID NO: 2); and
  c. a non-cyclized homolog of TL-1, having at least 70% sequence homology to SEQ ID NO: 1 and at least 70% of the electric characteristics of SEQ ID NO: 1, wherein the two adjacent cysteines at positions 5 and 6 of SEQ ID NO: 1 are retained.

In another embodiment, the homolog has at least 70% sequence homology to SEQ ID NO: 1. In another embodiment, the homolog has at least 70% identity with regard to the overall positive charge density of SEQ ID NO: 1. In another embodiment, the two adjacent cysteines at positions 5 and 6 of SEQ ID NO: 1 are retained. In another embodiment the homolog induces or enhances mobilization of hematopoietic progenitor and/or stem cells.

According to some embodiments, the invention is directed to a peptide of SEQ ID NO: 1 and homologs thereof having an N-terminus (N') and a C-terminus (C'). In other words, the N' and C' amino acids of these homologs are not interlinked by a covalent bond such as a peptide bond. The N' and C' may optionally be derivatized by stabilizing chemical groups as known in the art, which do not substantially affect the structure or conformation of the peptide, such as by amidation, acetylation, conjugation of fatty acids and the like. In other embodiments, the peptide or homolog has free (non-derivatized) N' and C' termini. In certain embodiments the peptide or homolog is linear or substantially linear. In other embodiments, the peptide or homolog does not contain loop regions formed e.g. by lactam bridges or by disulfide bonds. In the specification, the term "non-cyclized" may also be used to describe these peptides.

As used herein, the term "isolated peptide" refers to either a synthetic peptide or a peptide which has been "altered by the hand of man" and separated from the co-existing materials of its natural state. An isolated peptide has been synthetically produced or changed or removed from its original environment or both.

Whenever peptides are mentioned in the invention, also salts and functional derivatives thereof are contemplated, as long as they retain the biologic functions of the peptide, as detailed herein. Thus, the present invention encompasses peptide homologs containing non-natural amino acid derivatives or non-protein side chains. The peptide homologs of the invention may be used having a terminal carboxy acid, as a carboxy amide, as a reduced terminal alcohol or as any pharmaceutically acceptable salt, e.g., as metal salt, including sodium, potassium, lithium or calcium salt, or as a salt with an organic base, or as a salt with a mineral acid, including sulfuric acid, hydrochloric acid or phosphoric acid, or with an organic acid e.g., acetic acid or maleic acid. Generally, any pharmaceutically acceptable salt of the peptide of the invention may be used, as long as the biological activities of the peptide are maintained.

The amino acid residues described herein are preferred to be in the "L" isomeric form. However, residues in the "D" isomeric form can be substituted for any L-amino acid residue, as long as the peptide substantially retains the desired functional property.

In another embodiment, peptide homologs may be synthesized, said homologs being essentially based on the disclosed peptides as regards their amino acid sequence but having one or more amino acid residues deleted, substituted or added. When amino acid residues are substituted, such conservative replacements which are envisaged are those which do not significantly alter the structure or biological activity of the peptide. For example basic amino acids will be replaced with other basic amino acids, acidic ones with acidic ones and neutral ones with neutral ones. In addition to homologs comprising conservative substitutions as detailed above, peptide homologs comprising non-conservative amino acid substitutions are further envisaged, as long as said homologs essentially retain the biological activities of the peptides, as detailed herein. In another embodiment, the term "homolog" is directed to a peptide having at least 70%, preferably at least 80%, most preferably at least 90% sequence similarity to the amino acid sequence of the peptide in question, as defined, e.g., by the BLOSUM-80, 62 or 45 amino acid substitution matrices. It is well appreciated by the skilled artisan that the degree of homology may be calculated taking into account the overall length of the sequences being compared. Thus, peptide homologs of the invention exclude e.g. long polypeptide chains such as the wild type HBD3 molecule as well as very short peptides of 5 amino acids or less. Typically, a peptide homolog of the invention is 7 to 13 amino acids in length, 8 to 12 amino acids in length or 9 to 11 amino acids in length. The peptides of the invention include in some embodiments peptide homologs having 1-4 additional amino acids added to the N', to the C' or both, as long as the peptide properties with respect to charge and/or hydrophobicity are retained. Such extended peptides are generally up to about 16 amino acids in length.

The peptides of the invention preferably contain two cysteine residues, more typically two adjacent cysteine residues. For example, a peptide of 10 aa in length preferably contains cysteine residues at positions 5 or 6, and preferably at both positions. According to certain currently preferred embodiments, the cysteine residues are not disulfide bonded. According to other embodiments, the cysteine residues are disulfide bonded. In alternate embodiments, peptide homologs in which one or more of the cysteine residues has been substituted or modified (e.g. homocysteine residues) are contemplated.

The active peptides according to the invention are characterized as being highly charged, i.e. of strong electric properties (7 out of 10 constituent amino acid residues of TL-1 and AK-1 are positively charged) and hydrophilic. In another embodiment, a TL-1 homolog of the invention has at least 80% sequence homology (or identity) to SEQ ID NO: 1. In another embodiment, said TL-1 homolog has at least 90% sequence homology to SEQ ID NO: 1. In another embodiment, said TL-1 homolog has at least 80% of the electric characteristics of SEQ ID NO: 1. In another embodiment, said TL-1 homolog has at least 90% of the electric characteristics of SEQ ID NO: 1. In another embodiment, said TL-1 homolog has at least 70% identity with regard to the overall positive charge density of SEQ ID NO: 1 (wherein the phrase "charge density" as used herein refers to the number of charged groups in the peptide under physiological conditions). In another embodiment, said TL-1 homolog has at least 80% identity with regard to the overall positive charge density of SEQ ID NO: 1. In another embodiment, said TL-1 homolog has at least 90% identity with regard to the overall positive charge density of SEQ ID NO: 1. In another embodiment, said TL-1 homolog has at least 70% of the hydrophilicity/hydrophobicity characteristics of SEQ ID NO: 1. In another embodiment, said TL-1 homolog has at least 80% of the hydrophilicity/hydrophobicity characteristics of SEQ ID NO: 1. In another embodiment, said TL-1 homolog has at least 90% of the hydrophilicity/hydrophobicity characteristics of SEQ ID NO: 1. Each possibility represents a separate embodiment of the present invention.

In another embodiment, the peptide is a homolog of SEQ ID NO: 1, wherein one or more of the amino acids has been substituted for an amino acid having the same electric (charge), hydrophilicity/hydrophobicity and/or isosteric properties. For example, one or more arginine residues may be substituted for lysine or ornitine.

In another embodiment, a cyclic (or cyclized) homolog of the invention has at least 80% sequence homology (or identity) to SEQ ID NO: 3. In another embodiment, said cTL-1 homolog has at least 90% sequence homology to SEQ ID NO: 3. In another embodiment, said cTL-1 homolog has at least 80% of the electric characteristics of SEQ ID NO: 3. In another embodiment, said cTL-1 homolog has at least 90% of the electric characteristics of SEQ ID NO: 3. In another embodiment, said cTL-1 homolog has at least 70% identity with regard to the overall positive charge density of SEQ ID NO: 3. In another embodiment, said cTL-1 homolog has at least 80% identity with regard to the overall positive charge density of SEQ ID NO: 3. In another embodiment, said cTL-1 homolog has at least 90% identity with regard to the overall positive charge density of SEQ ID NO: 3. In another embodiment, said cTL-1 homolog has at least 70% of the hydrophilicity/hydrophobicity characteristics of SEQ ID NO: 3. In another embodiment, said cTL-1 homolog has at least 80% of the hydrophilicity/hydrophobicity characteristics of SEQ ID NO: 3. In another embodiment, said cTL-1 homolog has at least 90% of the hydrophilicity/hydrophobicity characteristics of SEQ ID NO: 3. Each possibility represents a separate embodiment of the present invention.

In another embodiment, the peptide is a cyclic (or cyclized) homolog of SEQ ID NO: 3, wherein one or more of the amino acids has been substituted for amino acid(s) having the same electric (charge), hydrophilicity/hydrophobicity and/or isosteric properties. For example, one or more arginine residues may be substituted for lysine or ornitine.

The polypeptides and peptides of the invention may be isolated or synthesized using any recombinant or synthetic method known in the art, including, but not limited to, solid phase (e.g. Boc or f-Moc chemistry) and solution phase synthesis methods. For example, the peptides can be synthesized by a solid phase peptide synthesis method of Merrifield (1963). Alternatively, a peptide of the present invention can be synthesized using standard solution methods well known in the art (see, for example, Bodanszky, 1984) or by any other method known in the art for peptide synthesis.

In alternate embodiments, the peptides may be produced by recombinant technology. Recombinant methods for designing, expressing and purifying proteins and peptides are known in the art (see, e.g. Sambrook et al., 1992). Nucleic acid molecules according to the invention may include DNA, RNA, or derivatives of either DNA or RNA. An isolated nucleic acid sequence encoding a peptide can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention. A polynucleotide or oligonucleotide sequence can be deduced from the genetic code of a protein, however, the degeneracy of the code must be taken into account, as well as the allowance of exceptions to classical base pairing in the third position of the codon, as given by the so-called "Wobble rules". Moreover, polynucleotides that include more or less nucleotides can result in the same or equivalent proteins. Thus, according to other embodiments, the invention provides nucleic acids encoding the peptides of the invention, as well as recombinant constructs, expression vectors and pharmaceutical compositions thereof as known in the art (see, e.g. Sambrook et al., 1992).

Pharmaceutical Compositions

In another aspect, the invention provides a pharmaceutical composition containing an effective amount of a peptide selected from SEQ ID NOs: 1 and 2 and homologs thereof as defined herein, and one or more pharmaceutically accepted carriers, excipients or diluents. In one embodiment, there is provided a pharmaceutical composition containing an effective amount of an isolated peptide having an N-terminus and a C-terminus, wherein the peptide is selected from the group consisting of:
  (a) RGRKCCRRKK (TL-1, SEQ ID NO: 1);
  (b) SGRKCCRKKK (AK-1, SEQ ID NO: 2); and
  (c) a homolog of TL-1, having at least 70% sequence homology to SEQ ID NO: 1, at least 70% of the electric characteristics of SEQ ID NO: 1, wherein the cysteines at positions 5 and 6 of SEQ ID NO: 1 are retained, and wherein said homolog induces or enhances mobilization of hematopoietic progenitor and/or stem cells;
and one or more pharmaceutically accepted carriers, excipients or diluents, said composition further comprising at least one agent which stimulates (or enhances) mobilization of hematopoietic cells.

In another aspect, the invention provides a pharmaceutical composition comprising an effective amount of a peptide as set forth in SEQ ID NO: 3 or a homolog thereof as defined herein and one or more pharmaceutically accepted carriers, excipients or diluents. In another embodiment, the peptide is a cyclized peptide selected from the group consisting of:
  (a) 1,10-cyclo[RGRKCCRRKK], (cTL-1, SEQ ID NO: 3), wherein the arginine at position 1 is linked through a peptide bond to the lysine at position 10; and
  (b) a cyclized homolog of SEQ ID NO: 3 having at least 70% sequence homology to SEQ ID NO: 3 and at least 70% identity with regard to the overall positive charge density of SEQ ID NO: 3, wherein the N-terminus and the C-terminus of the peptide are linked through a covalent bond, and wherein the two adjacent cysteines at positions 5 and 6 of SEQ ID NO: 3 are retained.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable", "physiologically suitable" and "pharmaceutically acceptable", which may be used interchangeably, when used to describe carriers, excipients or diluents, refer to such materials that do not cause significant irritation to an organism and does not abrogate the biological activity and properties of the administered compound.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences", Mack Publishing Co., Easton, Pa., which is herein fully incorporated by reference (Remington: The Science and Practice of Pharmacy, Gennaro, A., Lippincott, Williams & Wilkins, Philadelphia, Pa., $20^{th}$ ed, 2000).

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

The pharmaceutical compositions of the invention are suitable for administration systemically or in a local manner, for example, via injection of the pharmaceutical composition directly into a tissue region of a patient. In a particular embodiment, the peptides are administered by injection, e.g. subcutaneously.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

Pharmaceutical compositions suitable for use in the context of the present invention include compositions wherein the active ingredients are contained in an amount effective to achieve the intended purpose. Determination of a therapeutically effective amount is well within the capability of those skilled in the art, especially in light of the detailed disclosure provided herein. For example, without limitation, a concentration of 0.01-1000, 0.1-100 or 1-10 µM may be suitable for ex-vivo treatment of cells in some embodiments, and a dosage of 0.005-50, 0.05-50, 0.005-20, 0.05-10 or 0.5-5 mg/kg may in some embodiments be suitable for in vivo treatment of a human subject.

In other embodiments, a pharmaceutical composition according to the invention may further comprise one or more additional pharmaceutical agents, e.g. anti-cancer drugs or cytokines. In certain embodiments, the composition may further comprise, in addition to a peptide of the invention, one or more other agents that induce or enhance mobilization or growth factors affecting hematopoietic cells, e.g. stem cell factor (SCF). In some embodiments, the composition may contain at least one cytokine that stimulates mobilization of hematopoietic cells, for example or a colony-stimulating factor, e.g. granulocyte-colony stimulating factor (G-CSF) and granulocyte-macrophages colony stimulating factor (GM-CSF). Other agents which promote or stimulate mobilization are e.g. interleukin-3 (IL-3), GM-CSF/IL-3 fusion proteins, FLK-2/FLT-3 ligand, IL-6, IL-11, thrombopoietin (TPO), vascular endothelial growth factor (VEGF) and combinations thereof.

In another aspect, the invention provides a pharmaceutical composition comprising as active ingredients effective amounts of granulocyte-colony stimulating factor (G-CSF) and a peptide selected from SEQ ID NOs: 1 and 2 and homologs thereof as defined herein. In other embodiments, said composition consists essentially of G-CSF and a peptide selected from SEQ ID NOs: 1 and 2 and homologs thereof as defined herein. In a particular embodiment, said peptide is SEQ ID NO: 1. In another particular embodiment, said peptide is SEQ ID NO: 2.

In certain embodiments, the term "effective amount" denotes an amount (e.g. of a peptide of the invention) that is effective to mediate a desired effect. In some embodiments, the term "effective amount" of G-CSF may indicate an amount that is effective, when administered with a peptide of the invention as detailed herein, to mediate the desired effect, e.g. to elevate the levels of WBC in the blood.

The term G-CSF in the context of the present specification and claims is used in its broadest sense in view of a protein having the biological activity of G-CSF as understood by the skilled artisan and comprises polypeptides (either of natural or synthetic including recombinant origin, either modified or not) as defined and described (including their preparation and use) in the scientific literature and, e.g., in any of the following patent publications: DE 30 27 105, EP 169 566, EP 215 126, EP 237 545, EP 396 158, EP 220 520, EP 217 404, EP 230 980, EP 231 819, DE 37 23 781, EP 263 490, EP 344 796, EP 355 811, EP 373 679, EP 401 384, EP 456 812, EP 459 630, EP 459 516, EP 459 795, EP 243 153, EP 272 703, EP 331 186, EP 335 423, WO 93/15211.

The term G-CSF comprises, in addition to G-CSF of natural origin and naturally-occurring variants thereof, any G-CSF coded by a DNA sequence which upon expression by conventional methods in a prokaryotic or eukaryotic (and preferably heterologous) host cell yields a polypeptide product having at least a part of the primary structure, and one or more of the biological properties of naturally-occurring G-CSF, which structure and properties are as defined in EP 237 545. Prokaryotic expression may be accomplished using known prokaryotic vectors and hosts, and may yield a G-CSF of this invention which has the characteristics of a prokaryotic expression product (for example an unglycosylated G-CSF).

As stated above the term G-CSF comprises G-CSF, either of natural or recombinant origin, also in modified form, e.g., coupled to chemical entities which without altering the basic biological activity of G-CSF are capable of modifying it in a therapeutically advantageous way, for example by improving its stability or solubility, or reducing its immunogenicity. A preferred and well-known modification of polypeptides such as G-CSF is by coupling to water-soluble polymers, such as polyethylene glycols or polypropylene glycols, within a wide range of molecular weights, e.g., from 500 to 20,000 daltons. This coupling provides protected G-CSFs, e.g., pegylated G-CSF, which should be substantially non-immunogenic. Various methods of coupling the polymer with G-CSF via different known linkers are known in the art and available to a skilled person. For example, some are described in U.S. Pat. No. 4,179,337. Modified G-CSFs and their preparation are described in EP 401 384, EP 335 423 and EP 473 268. Modified G-CSF also comprises G-CSF which shows a different glycosylation pattern than that known for naturally occurring or recombinant G-CSF, in particular by the addition of at least one polycarbohydrate chain as described in EP 370 205.

Examples of commercially available recombinant human G-CSF include filgrastim (Gran® and Neupogen®), lenograstim (Neutrogin® and Granocyte®) and nartograstim (Neu-up®).

In another aspect, there is provided a kit comprising i) at least one cytokine that stimulates mobilization of hematopoietic cells, preferably G-CSF, and ii) a peptide selected from SEQ ID NOs: 1 and 2 and homologs thereof as defined herein.

In one embodiment, there is provided a pharmaceutical pack containing a course of treatment for one individual mammal comprising a container having a unit of a peptide selected from SEQ ID NOs: 1 and 2 and homologs thereof as defined herein in unit dosage form, and a container having a unit of G-CSF.

In another embodiment, there is provided a kit comprising a peptide of the invention and an anti-cancer drug.

In a particular embodiment, there is provided a kit comprising i) a peptide selected form SEQ ID NOs: 1 and 2 and homologs thereof as defined herein and ii) an anti-cancer drug.

In another particular embodiment, there is provided a pharmaceutical pack containing a course of treatment for one individual mammal comprising a container having a unit of a peptide selected from SEQ ID NOs: 1 and 2 and homologs thereof as defined herein in unit dosage form, and a container having a unit of an anti-cancer drug.

In another embodiment, there is provided a kit comprising i) a peptide selected form SEQ ID NOs: 3 and homologs thereof as defined herein and ii) an anti-cancer drug.

In some embodiments, the combinations of the invention are provided in packs in a form ready for administration. In other embodiments, the combinations of the invention are provided in concentrated form in packs, optionally with the diluent required to make final solution(s) for administration. In still other embodiments, the product contains a compound useful in the invention in solid form and, optionally, a separate container with a suitable solvent or carrier for the compound useful in the invention.

In still other embodiments, the above packs/kits include other components, e.g., instructions for dilution, mixing and/or administration of the product, other containers, syringes, needles, etc. Other such pack/kit components will be readily apparent to one of skill in the art.

Therapeutic Use

According to some embodiments, the invention provides methods for modulating mobilization and/or homing of hematopoietic cell populations. For example, in some embodiments, the peptides of SEQ ID NOs: 1 and 2 were found to enhance leukocyte mobilization from the bone marrow to peripheral blood and to enhance HSPC homing to the bone marrow, while SEQ ID NO: 3 has been found to inhibit homing of malignant cells to the bone marrow.

In another aspect, the invention provides a method for elevating the levels of hematopoietic cells in peripheral blood of a subject comprising administering to the subject an effective amount of a peptide selected from SEQ ID NOs: 1 and 2 and homologs thereof as defined herein. In some embodiments, the method may be used to elevate the levels of hematopoietic progenitor and/or stem cells (HSPC) in peripheral blood, e.g. for mobilizing and subsequent harvesting HSPC for bone marrow transplantation. In certain embodiments, the peptide may be administered to said subject in combination with one or more agents used to induce mobilization of white blood cells, e.g. with at least one cytokine that stimulates mobilization of hematopoietic cells. In one embodiment, the peptides of the invention are administered in combination with G-CSF or an analog or derivative thereof. In another embodiment, the peptide is TL-1 (SEQ ID NO: 1). In another embodiment, the peptide is AK-1 (SEQ ID NO: 2).

The term "hematopoietic cell" as used herein refers to any type of cell of the hematopoietic system, including, but not limited to, undifferentiated cells such as hematopoietic stem cells and progenitor cells, and differentiated cells e.g. leukocytes (for example granulocytes, monocytes and lymphocytes).

The term "hematopoietic stem cell" is used in the broadest sense to refer to stem cells from which blood cells derive, including pluripotent stem cells, lymphoid and myeloid stem cells.

The term "hematopoietic progenitor cell" refers to the progeny of a pluripotent hematopoietic stem cell which are committed for a particular line of differentiation. These committed progenitor cells are irreversibly determined as ancestors of only one or a few blood cell types, e.g. erythrocytes, megakaryocytes, monocytes or granulocytes.

The term "hematopoietic precursor cell" as used herein includes hematopoietic stem cells, hematopoietic progenitor cells or any cell which gives rise to a cell in the hematopoietic lineages (e. g., lymphoid, myeloid). In a particular embodiment, the cells are CD34$^+$ cells (characterized by surface expression of the CD34 marker, including CD34$^+$/CD38$^{-/low}$ cells). In another embodiment, the hematopoietic precursor cells are CXCR4$^+$ cells.

In another aspect, the invention provides a method for obtaining a therapeutically effective amount of hematopoietic precursor cells from a subject, comprising:
  a) administering to the subject a peptide selected from SEQ ID NOs: 1 and 2 and homologs thereof as defined herein in an amount sufficient to elevate the levels of hematopoietic precursor cells in peripheral blood of the subject;
  b) harvesting said precursor cells (obtaining the cells from peripheral blood of said subject, e.g. by apheresis); and optionally
  c) repeating steps (a) and (b) until a therapeutically effective amount of hematopoietic precursor cells is obtained.

In one embodiment, the peptide is administered in combination with G-CSF. In another embodiment, the peptide is TL-1 (SEQ ID NO: 1). In another embodiment, the peptide is AK-1 (SEQ ID NO: 2).

In another aspect, there is provided a method for engrafting hematopoietic precursor cells in a patient in need of hematopoietic precursor cell transplantation, comprising the steps of:
a) administering to a donor subject a peptide selected from SEQ ID NOs: 1 and 2 and homologs thereof as defined herein in an amount sufficient to elevate the levels of hematopoietic precursor cells in peripheral blood of the subject;
b) harvesting hematopoietic precursor cells from peripheral blood of said subject (e.g. by apheresis);
c) optionally repeating steps (a) and (b) until a therapeutically effective amount of hematopoietic precursor cells is obtained; and
d) transplanting the resulting cells into a recipient patient in need thereof.

In one embodiment, the donor subject and the recipient patient are the same (i.e. when performing an autologous transplantation). In another embodiment, the donor subject and the recipient patient are not the same (i.e. when performing an allogeneic transplantation). It is generally accepted in the art that an allogeneic donor should preferably be sufficiently histocompatible with the recipient patient so as to avoid or minimize graft rejection. Optionally, the method further comprises administering to the recipient patient a peptide selected from SEQ ID NOs: 1 and 2 and homologs thereof as defined herein, in an amount sufficient to enhance engraftment of said cells. In one embodiment, the peptide is administered in combination with G-CSF. In another embodiment, the peptide is TL-1 (SEQ ID NO: 1). In another embodiment, the peptide is AK-1 (SEQ ID NO: 2).

In another embodiment, the invention provides a method for enhancing engraftment of HSPC in a subject undergoing HSPC transplantation, comprising contacting the cells with (e.g. by administering to said subject) a peptide selected from SEQ ID NOs: 1 and 2 and homologs thereof as defined herein, in an amount sufficient to enhance engraftment of said cells.

In another aspect, there is provided a method of increasing G-CSF-induced hematopoietic precursor cell mobilization, comprising administering to a subject an effective amount of G-CSF in concurrent or sequential combination with a peptide selected from SEQ ID NOs: 1 and 2 and homologs thereof as defined herein. In another embodiment, the peptide is TL-1 (SEQ ID NO: 1). In another embodiment, the peptide is AK-1 (SEQ ID NO: 2).

In other embodiments, the peptides of the invention are used for mobilizing malignant hematopoietic cells from the bone marrow or other tissue sites, thus improving their accessibility to cancer therapy (e.g. to conventional chemotherapy protocols). Thus, in another aspect, there is provided a method of inducing mobilization of malignant hematopoietic cells, comprising administering to a subject an effective amount of a peptide selected from SEQ ID NOs: 1 and 2 and homologs thereof as defined herein. In another embodiment, the peptide is TL-1 (SEQ ID NO: 1). In another embodiment, the peptide is AK-1 (SEQ ID NO: 2). In certain embodiments, the subject is afflicted with a CXCR4 expressing tumor, responding to SDF-1.

In another aspect, there is provided a method for treating cancer in a subject in need thereof, comprising: 1) administering to the subject an effective amount of a peptide selected from SEQ ID NOs: 1 and 2 and homologs thereof as defined herein; and 2) administering to said subject an effective amount of a cancer therapy. In another embodiment, the cancer is of hematopoietic origin. In another embodiment, the cancer is characterized by CXCR4 expression of at least a portion of the cancer cells. In another embodiment the cancer is a CXCR4 expressing cancer, responding to SDF-1. In another embodiment, the peptide is TL-1 (SEQ ID NO: 1). In another embodiment, the peptide is AK-1 (SEQ ID NO: 2). In some embodiments, the cancer therapy is chemotherapy, radiotherapy or immunotherapy.

In other embodiments, the invention is directed to the use of an isolated peptide having an N-terminus and a C-terminus, wherein the peptide is selected from the group consisting of:
(a) RGRKCCRRKK (TL-1, SEQ ID NO: 1);
(b) SGRKCCRKKK (AK-1, SEQ ID NO: 2); and
(c) a homolog of TL-1, having at least 70% sequence homology to SEQ ID NO: 1 and at least 70% identity with regard to the overall positive charge density of SEQ ID NO: 1, wherein the two adjacent cysteines at positions 5 and 6 of SEQ ID NO: 1 are retained, and wherein said homolog induces or enhances mobilization of hematopoietic progenitor and/or stem cells;

for the preparation of a medicament for: elevating the levels of hematopoietic cells in peripheral blood of a subject; obtaining a therapeutically effective amount of hematopoietic precursor cells from a subject; engrafting hematopoietic precursor cells in a patient in need of hematopoietic precursor cell transplantation; enhancing engraftment of HSPC in a subject undergoing HSPC transplantation; increasing G-CSF-induced hematopoietic precursor cell mobilization; inducing mobilization of malignant hematopoietic cells and/or treating cancer in a subject in need thereof, wherein each possibility represents a separate embodiment of the invention.

In another embodiment, the invention provides a method for elevating the levels of hematopoietic cells in peripheral blood of a subject comprising administering to the subject an effective amount of an isolated peptide having an N-terminus and a C-terminus, wherein the peptide is selected from the group consisting of:
(a) RGRKCCRRKK (TL-1, SEQ ID NO: 1);
(b) SGRKCCRKKK (AK-1, SEQ ID NO: 2); and
(c) a homolog of TL-1, having at least 70% sequence homology to SEQ ID NO: 1, at least 70% identity with regard to the overall positive charge density of 'SEQ ID NO: 1, wherein the cysteines at positions 5 and 6 of SEQ ID NO: 1 are retained, and wherein said homolog induces or enhances mobilization of hematopoietic progenitor and/or stem cells.

In another embodiment, the cells are hematopoietic precursor cells and the method comprises the steps of:
a) administering the peptide to said subject, in an amount sufficient to elevate the levels of hematopoietic precursor cells in peripheral blood of said subject;
b) harvesting hematopoietic precursor cells from peripheral blood of said subject; and optionally
c) repeating steps a) and b) until a therapeutically effective amount of hematopoietic precursor cells is obtained;
thereby obtaining a therapeutically effective amount of hematopoietic precursor cells from said subject.

In an additional embodiment, said method may further comprise the step of transplanting the harvested cells (resulting from step b), or from step c) when applicable) into a recipient patient in need of hematopoietic precursor cell transplantation, thereby engrafting hematopoietic precursor cells in the patient.

Optionally, the cells may be further contacted with the peptide prior to transplantation, thereby enhancing their engraftment in the recipient subject. In a particular embodiment, the contacting is performed ex vivo. In another embodiment, the contacting is performed in vivo.

In another embodiment, the cells are malignant hematopoietic cells and the method is used for inducing (or enhancing) mobilization of malignant hematopoietic cells in the subject. In a particular embodiment, the method further comprises administering to said subject an effective amount of a cancer therapy, thereby treating cancer in said subject.

In another embodiment, there is provided a method for enhancing engraftment of HSPC in a subject undergoing HSPC transplantation, comprising administering to the subject a peptide in an amount sufficient to enhance engraftment of said cells, wherein said peptide is an isolated peptide having an N-terminus and a C-terminus, wherein the peptide is selected from the group consisting of:
  (a) RGRKCCRRKK (TL-1, SEQ ID NO: 1);
  (b) SGRKCCRKKK (AK-1, SEQ ID NO: 2); and
  (c) a homolog of TL-1, having at least 70% sequence homology to SEQ ID NO: 1, at least 70% identity with regard to the overall positive charge density of SEQ ID NO: 1, wherein the cysteines at positions 5 and 6 of SEQ ID NO: 1 are retained, and wherein said homolog induces or enhances mobilization of hematopoietic progenitor and/or stem cells.

In another embodiment, the invention provides a method of increasing G-CSF-induced hematopoietic precursor cell mobilization, comprising administering to a subject an effective amount of G-CSF in concurrent or sequential combination with an isolated peptide having an N-terminus and a C-terminus, wherein the peptide is selected from the group consisting of:
  (a) RGRKCCRRKK (TL-1, SEQ ID NO: 1);
  (b) SGRKCCRKKK (AK-1, SEQ ID NO: 2); and
  (c) a homolog of TL-1, having at least 70% sequence homology to SEQ ID NO: 1, at least 70% identity with regard to the overall positive charge density of SEQ ID NO: 1, wherein the cysteines at positions 5 and 6 of SEQ ID NO: 1 are retained, and wherein said homolog induces or enhances mobilization of hematopoietic progenitor and/or stem cells.

In certain embodiments, the methods for elevating the levels of hematopoietic cells in peripheral blood of a subject, for obtaining a therapeutically effective amount of hematopoietic precursor cells from a subject, and for engrafting hematopoietic precursor cells in a patient in need of hematopoietic precursor cell transplantation may optionally be performed by administration of a pharmaceutical composition containing an effective amount of a peptide selected from SEQ ID NOs: 1 and 2 and homologs thereof as defined herein, and further comprising one or more agents which stimulate mobilization of hematopoietic cells, e.g. G-CSF.

In another aspect, the invention provides a method for reducing or inhibiting cancer metastasis in a subject in need thereof, comprising administering to the subject an effective amount of a peptide as set forth in SEQ ID NO: 3 or a homolog thereof as defined herein. In one embodiment, the invention provides a method for reducing or inhibiting cancer metastasis in a subject in need thereof, comprising administering to the subject an effective amount of a cyclized peptide selected from the group consisting of:
  (a) 1,10-cyclo[RGRKCCRRKK], (cTL-1, SEQ ID NO: 3), wherein the arginine at position 1 is linked through a peptide bond to the lysine at position 10; and
  (b) a cyclized homolog of SEQ ID NO: 3 having at least 70% sequence homology to SEQ ID NO: 3 and at least 70% identity with regard to the overall positive charge density of SEQ ID NO: 3, wherein the N-terminus and the C-terminus of the peptide are linked through a covalent bond, and wherein the two adjacent cysteines at positions 5 and 6 of SEQ ID NO: 3 are retained.

In another embodiment, the subject is afflicted with a tumor characterized by CXCR4 expression of at least a portion of the tumor cells. In another embodiment, said tumor is of hematopoietic origin. In a particular embodiment, said tumor is leukemia. In another embodiment the cancer is a CXCR4 expressing cancer, responding to SDF-1. In another embodiment, the method is used for preventing cancer metastasis. In another embodiment, the method is used for reducing the incidence of cancer metastasis. In other embodiments, the method may be used for reducing the number or size of metastatic foci or for delaying the onset of cancer metastasis, wherein each possibility represents a separate embodiment of the invention.

In another aspect, the invention provides a method for reducing or inhibiting migration or homing of CXCR4-expressing malignant cells to the bone marrow of a subject in need thereof, comprising contacting the cells with an effective amount of a peptide as set forth in SEQ ID NO: 3 or a homolog thereof as defined herein. In one embodiment, the invention provides a method for reducing or inhibiting migration or homing of CXCR4-expressing malignant cells to the bone marrow of a subject in need thereof, comprising contacting the cells with an effective amount of a cyclized peptide selected from the group consisting of:
  (a) 1,10-cyclo[RGRKCCRRKK], (cTL-1, SEQ ID NO: 3), wherein the arginine at position 1 is linked through a peptide bond to the lysine at position 10; and
  (b) a cyclized homolog of SEQ ID NO: 3 having at least 70% sequence homology to SEQ ID NO: 3 and at least 70% identity with regard to the overall positive charge density of SEQ ID NO: 3, wherein the N-terminus and the C-terminus of the peptide are linked through a covalent bond, and wherein the two adjacent cysteines at positions 5 and 6 of SEQ ID NO: 3 are retained.

In one embodiment, the contacting is performed in vivo. In another embodiment, the contacting is performed ex vivo. In another embodiment, said malignant cells are of hematopoietic origin. In a particular embodiment, said malignant cells are leukemic cells. In another embodiment the cells are CXCR4 expressing cells, responding to SDF-1.

In other embodiments, the invention is directed to the use of a cyclized peptide selected from the group consisting of:
  (a) 1,10-cyclo[RGRKCCRRKK], (cTL-1, SEQ ID NO: 3), wherein the arginine at position 1 is linked through a peptide bond to the lysine at position 10; and
  (b) a cyclized homolog of SEQ ID NO: 3 having at least 70% sequence homology to SEQ ID NO: 3 and at least 70% identity with regard to the overall positive charge density of SEQ ID NO: 3, wherein the N-terminus and the C-terminus of the peptide are linked through a covalent bond, and wherein the two adjacent cysteines at positions 5 and 6 of SEQ ID NO: 3 are retained;
for the preparation of a medicament for reducing or inhibiting cancer metastasis in a subject in need thereof and/or for reducing or inhibiting migration or homing of CXCR4-expressing malignant cells to the bone marrow of a subject in need thereof, wherein each possibility represents a separate embodiment of the invention. In a particular embodiment the sequence of the peptide is as set forth in SEQ ID NO: 3.

In the methods of the invention, the peptides may optionally be administered alone or in the form of a pharmaceutical composition further comprising one or more pharmaceutically acceptable carriers, excipients or diluents.

Common procedures for harvesting, purifying and transplanting stem cells and progenitor cells in suitable recipient subjects are well known in the art and are employed in the methods of the invention (see, for example, Devine et al., 2008). For example, for harvesting of hematopoietic cells (including precursor cells) apheresis (or leukophoresis) may be carried out with the Cobe Spectra (Gambra), Hemonetics (Domediac), Amicus (Baxter) or equivalent equipment, according to protocols known in the art. Apheresis typically results in a leukocyte population highly enriched in mononuclear cells and depleted for granulocytes. If insufficient HSPC are obtained from a first series of mobilization/apheresis (e.g. less than $1.63*10^6$ CD34$^+$ cells per kg of body weight of the human subject), the procedure can be repeated with the same or modified mobilization regime. Alternatively, apheresis can be repeated. Cells obtained from the first procedure can be cryopreserved and combined with those from subsequent procedures. HSPC cells may be collected by apheresis on days 3, 4, 5, 6 or later after beginning the administration of the mobilizing agent. In some embodiments, CD34$^+$ cells may be selected by any of the clinical grade devices known in the art such as the Isolex 300i cell selection system or the CEPRATE SC Stem Cell Concentration System. Optionally, the cells are further purged to remove unwanted cells, e.g. to remove malignant cells for autologous transplantations in cancer patients, using methods well known in the art.

Any methods including quantitative and qualitative methods can be used to identify that the hematopoietic stem cells have been mobilized into the peripheral blood. The methods typically involve isolating a quantity of the patient's blood and analyzing the quantity of the cells within the blood. Any method can be used to analyze the number of cells, including but not limited to: FACS analysis, coulter counters and other blood counting devices, morphological identification, and PCR. The cells can be identified by any method known to one of skill in the art, including but not limited to, the identification of one or more proteins which are specifically expressed by the stem cells, by morphology, by mRNA expression, and by PCR.

In some embodiments, the methods may further comprise a step of culturing the isolated cells in the presence of therapeutic or modulatory agents, e.g. cytokines or a cytokine mixture, prior to administering them to the recipient patient. In other embodiments, the cells may be modified by gene therapy or otherwise altered or conditioned before transplantation and engraftment.

Transplantation of the cells may be performed according to protocols known in the art. In an embodiment of the invention, the composition is formulated to be ready for delivery into a human subject. The great majority of cells should be viable, for example greater than 95% or greater than 98%. The volume of the composition is typically from about 10 ml to about 1000 ml or from about 100 ml to about 500 ml. The composition comprises a pharmaceutically acceptable carrier e.g. a buffered salts solution comprising a protein agent such as an albumin or gelatine and/or a sugar such as glucose, which agents may act to stabilize the cells. The carrier may contain anticoagulant agents such as sodium citrate. The carrier may comprise a plasma expander, well known in the art. In further aspects, the composition is sterile (bacterial, fungal, *mycoplasma*), detectably free of bacteria, endotoxin, *mycoplasma*, HIV p24 antigen or replication-competent retrovirus, or any combination of these. In a further embodiment, the composition is substantially free of added cytokines. In another embodiment, the composition further comprises a peptide selected from SEQ ID NOs: 1 and 2 and homologs thereof as defined herein. The composition is typically administered to the subject by parenteral means, preferably by infusion or injection on one or more occasions.

The term "mobilization" refers to the process whereby cells leave the bone marrow and enter the blood. The term "homing" refers to the in vivo activity of a cell, and specifically to the preferential movement and/or accumulation of the cell in a target tissue, e.g. the bone marrow or spleen, as compared to a control tissue. In some embodiments, the present invention refers to modulating the homing of CXCR4 expressing cells to the bone marrow. The term "engrafting" or "engraftment" means the persistence of precursor cells in a particular location over time. In some embodiments, engraftment depends, among other processes, on the migration or homing of these cells to the location, such as to the bone marrow. In a particular embodiment, peptides of the invention may be used for promoting long term engraftment of HSPC in the bone marrow of a patient.

In some embodiments, the present invention is directed to methods for providing improved hematopoietic precursor cell transplantation, for example for the treatment of patients whose bone marrow has been depleted e.g. by irradiation or chemotherapy. For example, the peptides may be used on cancer patients undergoing cancer associated chemotherapy and/or bone marrow transplantation and patients with irradiation injuries. In some embodiments, hematopoietic stem cell transplantation (HSCT) protocols may for example be utilized for the purpose of treating the following diseases: Aplastic Anemia; Acute Lymphoblastic Anemia.; Acute Myelogenous Leukemia; Myelodysplasia; Multiple Myeloma; Chronic Lymphocytic Leukemia; Congenital Immunodeficiencies (such as Autoimmune Lymphoproliferative disease, Wiscott-Aldrich Syndrome, X-linked Lymphoproliferative disease, Chronic Granulamatous disease, Kostmann Neutropenia, Leukocyte Adhesion Deficiency); Metabolic Diseases (for instance those which have been HSCT indicated such as Hurler Syndrome (MPS I/II), Sly NW Syndrome (MPS VII), Chilhood onset cerebral X-adrenoleukodystrophy, Globard_cell Leukodystrophy).

In other embodiments, the peptides of the invention are used in the treatment of cancer patients, optionally in conjunction with additional cancer therapy, as detailed herein. Protocols for cancer therapy, e.g. chemotherapy, radiotherapy or immunotherapy are well known in the art and may be selected by the skilled artisan according to the type of cancer and the specific patient. In some embodiments, the chemotherapy includes but is not limited to alkylating agents, antimetabolites and antibiotic agents. Exemplary chemotherapeutic compounds which may be used in the methods of the invention include carmustine, etoposide, cytarabine, melphalan, cyclophosphamide, busulfan, thiotepa, bleomycin, platinum (cisplatin), cytarabine, cyclophosphamide, buside, Cytoxan, daunorubicin, doxorubicin, agent ara-C, cyclosporin; Rituxan®; thalidomide; clofarabine; Velcade®; Antegren®; Ontak®; Revlimid® (thalidomide analog); Prochymal™; Genasense® (oblimersen sodium); Gleevec™ (imatinib); tamibarotene; nelarabine; gallium nitrate; PT-100; Bexxar®; Zevalin®; pixantrone; Onco-TCS; and agents that are topoisomerase inhibitors, and many others. In other embodiments, additional cytotoxic drugs may be used in the compositions and methods of the invention, including, but not limited to, taxol, 5-fluorouracil, adriamycin, methotrexate, cytosine arabinoside, mitomycin C, prednisone, vindesine, carbaplatinum, and vincristine. Each possibility represents a separate embodiment of the invention.

Some embodiments disclosed herein relate to an improved radiation therapy, wherein a peptide of the invention is provided before, during, or after a radiation therapy. Embodiments disclosed herein are not limited by the types, amounts, or delivery and administration systems used to deliver the therapeutic dose of radiation to a subject. For example, the subject may receive photon radiotherapy, particle beam radiation therapy, other types of radiotherapies, and combinations thereof. In some embodiments, the radiation is delivered to the subject using a linear accelerator. In still other embodiments, the radiation is delivered using a gamma knife, and in others, the radiation administered in the form of a radioactive implantable pellet.

In various embodiments, the terms "subject" and "patient" are intended to include human and non-human mammals. In a particular embodiment, the subject (or patient) is human. In some embodiments, subjects may include a human patient having a disorder, in which cells that express CXCR4, e.g. cancer cells, contribute to the etiology or pathology of the disorder. In other embodiments, the subject is in need of bone marrow transplantation and/or HPSC harvesting.

In some embodiments of the methods of the invention, hematopoietic tumors may include for example lymphoma, leukemia, myeloma or other malignancies of a lymphoid or myeloid origin. For example, without limitation, CXCR4-related hematopoietic tumors (or cancer) include non-Hodgkin's lymphoma, acute lymphocytic leukemia (ALL), chronic lymphocytic leukemia (CLL), acute myeolgenous leukemia (AML), Burkitt's lymphoma, anaplastic large-cell lymphomas (ALCL), multiple myeloma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers and diffuse large cell lymphomas of B lineage, wherein each possibility represents a separate embodiment of the invention.

Additionally, in some embodiments, the tumor (or cancer) is a CXCR4-expressing tumor of a non-hematopoietic origin, e.g. breast, prostate, colon, melanoma, tongue, ovarian, small and non-small cell lung tumors, pancreatic, esophageal, head and neck and bladder tumors, osteosarcoma and neuroblastoma. In other embodiments, the tumor is a metastasizing tumor or an SDF-1 dependent tumor (in which the growth and/or spreading is enhanced by SDF-1). Each possibility represents a separate embodiment of the invention.

Examples of dosage ranges that can be administered to a subject can be chosen from: 0.005-50, 0.05-50, 0.005-20, 0.05-10 or 0.5-5 mg/kg (or subranges thereof). These dosages may be administered daily, weekly, biweekly, monthly, or less frequently, depending on dosage, method of administration, disorder or symptom(s) to be treated, and individual subject characteristics. Dosages can also be administered via continuous infusion (such as through a pump). The administration of said compositions can be typically achieved by means of parenteral administration, e.g., intravenously (i.v.) subcutaneous (s.c.) or intramuscularly (i.m.). For instance, a dose of 1-20 mg/kg may be administered (e.g. by intravenous or subcutaneous injection) daily or twice a week to human patients, or a dose of 1-10 mg/kg may be administered by infusion or subcutaneous injection.

The peptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

As used herein, "treating" a disease or condition (or treating a subject with a disease, e.g. cancer) refers to taking steps to obtain beneficial or desired results, including but not limited to, alleviation or amelioration of one or more symptoms of the disease, diminishment of extent of disease, delay or slowing of disease progression, amelioration, palliation or stabilization of the disease state, partial or complete remission, prolonged survival and other beneficial results known in the art.

As used herein, the terms "inhibiting" or "reducing" refer to either statistically significant inhibition or reduction, or to inhibition or reduction to a significant extent as determined by a skilled artisan, e.g. the treating physician. It should be understood, that inhibition or reduction does not necessarily indicate a total elimination of the measured function or biological activity. A reduction in activity may be for example about 10%, 20%, 30%, 40%, 50%, 60%, 70%, 80%, 90%, or more.

The terms "elevating", "enhancing", and "increasing" refer to either statistically significant effects, or to elevation, enhancement or increase to a significant extent as determined by a skilled artisan, e.g. the treating physician. An elevation, enhancement or increase in activity may be for example of about 10%, 20%, 30%, 40%, 50%, 60%, 70%, 80%, 90%, or more.

The following examples are presented in order to more fully illustrate some embodiments of the invention. They should, in no way be construed, however, as limiting the broad scope of the invention.

EXAMPLES

Materials and Methods

Peptides.

Synthetic peptides having an amino acid sequence as set forth in SEQ ID NOs: 1-3 were prepared by automated solid phase synthesis.

Cells.

Freshly isolated primary human CD3$^+$ T cells, human myeloid HL-60 and U937 cell lines, human pre-B-ALL G2 cells, mouse stroma MS-5 and MBA-15 cells, and human osteosarcoma MG-63 cells were cultivated in corresponding tissue culture media, with 10% FCS, L-glutamin and antibiotics as previously described (Spiegel, A., et al., 2004, Kalinkovich, A., et al., 2006). Human cord blood (CB) cells from full term deliveries were separated on Ficoll-Paque (Pharmacia Biotech, Uppsala, Sweden). CD34$^+$ cells were enriched using the MACS cell isolation kit and the auto MACS magnetic cell sorter (Miltenyi Biotec, Bergisch Gladbach, Germany) according to the manufacturer's instructions, obtaining purity of >90% (Goichberg, P., et al., 2006, Kalinkovich, A., et al., 2006).

Mice.

C57BL/6 mice were purchased from Harlan (Israel). NOD/SCID (NOD/LtSzPrKdc$^{scid}$/PrKdc$^{scid}$) mice were bred and maintained under specific pathogen-free conditions at the animal facilities of the Weizmann Institute. The Weizmann Institutional Animal Care and Use Committee approved all animal experiments.

Cell Toxicity Assay.

Pre-B-ALL G2 cells and freshly isolated primary human $CD3^+$ T cells ($1\times10^6$/ml) were cultured in 96-well flat-bottom wells in serum free IMDM or RPMI 1640 medium, respectively, both supplemented with L-glutamine and antibiotics, for 6 and 24 hrs at 37° C. (95% humidity, 5% $CO_2$) with 10 µM, 100 µM or 1 mM of the peptides. Untreated cells served as a control. Cell viability was determined by propidium iodide (PI) exclusion by flow cytometry as described (Goichberg, P., et al., 2006).

ELISA.

SDF-1 levels in tested samples were determined by ELISA as described (Kalinkovich, A., et al., 2006) where the K15C monoclonal antibodies (mAb, INRA, Paris, France) recognizing the first three amino acids of SDF-1 were utilized as a capture Ab (10 µg/mL) in order to measure levels of intact, non-cleaved SDF-1. Levels of basic FGF (bFGF) and HGF in tested samples were determined by using corresponding capture mAbs and polyclonal biotynilated Abs (R&D Systems) as recommended by the manufacturer. In order to examine SDF-1, bFGF and HGF levels in cell supernatants, MS-5, MBA-15 and MG-63 cells were seeded in 24-well Costar wells and cultivated in RPMI 1640 or αMEM Eagle medium, respectively, with 10% FCS. When the cells reached confluence, the medium was changed to serum free medium and cells were cultivated for additional 6 hrs in the presence of various concentrations of the peptides. Medium samples were collected and centrifuged 10 min at 6000×g at 4° C. to remove cell debris. Supernatants were collected and kept at −70° C. until tested.

Transwell Migration and Chemotaxis Assays.

Various cells ($1\times10^6$/mL), untreated or pretreated with peptides for 3 hrs at 96-well flat bottom plates at 37° C. were washed, $2\times10^5$ cells/100 µL were added to the upper chambers of Costar 24-well transwell plates with 5 µm pore filters (Corning Inc., Corning, N.Y.) and allowed to migrate for 2-4 hrs at 37° C. (95% humidity, 5% $CO_2$) spontaneously or towards 50 ng/mL SDF-1 (rhSDF-1, Peprotech, Rocky Hill, N.J.) in medium supplemented with 10% FCS. In the chemotaxis assay, untreated cells were added to the upper chambers and the peptides were added to the lower chambers in serum free medium. Migrated cells were collected from the lower chambers and counted using a flow cytometer. Data are presented as a percentage of migrated cells.

Mobilization Assay.

C57BL/6 mice were injected s.c. with PBS (control), 5 mg/kg AMD3100, or one of the peptides TL-1, cyclic TL-1 and AK-1, at various doses. Another group of mice was s.c. injected with 5 mg/kg AMD3100 together with TL-1, or cyclic TL-1, or AK-1 (all peptides at 5 mg/kg), 1-1.5 hr before sacrifice. An additional group of mice was s.c. injected with-G-CSF at a dose of 5 µg/mouse once a day for 5 days. Mice were sacrificed 4 hrs post last G-CSF injection; 1-1.5 before sacrifice, mice were injected with TL-1, cyclic TL-1 or AK-1, all at 5 mg/kg. Peripheral blood (PB) was collected from mice by cardiac puncture into heparin containing tubes and the number of white blood cells (WBC) per 1 mL of blood was calculated. The tubes were centrifuged, plasma was collected and kept at −20° C. until tested. In order to evaluate the number of progenitor cells, PB mononuclear cells were isolated using Ficoll gradient centrifugation, and seeded ($2\times10^5$ cells/plate) in methylcellulose with cytokines as described (Spiegel, A., et al., 2004, Goichberg, P., et al., 2006). Colonies, reflecting colony-forming units (CFU), were scored after 7 days.

Homing Assay.

G2 cells ($10\times10^6$/mL) pretreated with the peptides for 3 hrs as described above, were injected i.v. into non-irradiated NOD/SCID mice, which were sacrificed 16 hrs later. Samples of BM cells flushed from both femur and tibia bones and spleen cell suspension were prepared, and the percentage of human cells was determined by staining with anti-human CD45-FITC mAb (ImmunoQuality Products, Groningen, The Netherlands) as described (Spiegel, A., et al., 2004).

Flow Cytometry Analysis.

Various cell types ($1\times10^6$/mL) were pretreated with the peptides for 3 hrs as described above, washed and then stained in staining buffer (PBS supplemented with 0.5% FCS and 0.01% sodium azide) with mouse anti-human CXCR4-PE, CCR5-FITC (R&D Systems, Minneapolis, Minn.) or CD45-FITC (ImmunoQuality Products, Groningen, The Netherlands) mAbs for 30 min at 4° C. and analyzed by flow cytometry as described (Kalinkovich, A., et al., 2006). Appropriate IgG were used as the isotype controls.

Zymography.

Gelatin zymography applied for determination of matrix metalloproteinases 2 and 9 (MMP2/9) in the supernatants collected from MS-5 cells preincubated with the peptides for 6 hrs as described above was performed as described (Spiegel, A., et al., 2004).

Statistical Analysis.

Data were analyzed using a two-tailed Student's t-test assuming unequal variances by Excel 2004. Values with $P<0.05$ were considered statistically significant.

Example 1

Effect of the Peptides on Cell Viability

In order to test cytotoxicity of the peptides, human pre-B-ALL G2 cells and freshly isolated primary human $CD3^+$ T cells ($1\times10^6$/ml) were cultured in with 10 µM, 100 µM or 1 mM of TL-1, AK-1 and cyclic TL-1, as described in the Material and Methods. All tested peptides were not toxic for G2 cells (FIG. 1) as well as for primary human T cells at 10 µM and 100 µM. Even in the highest concentration, 1 mM, the peptides killed only 8-12% and 14-16% cells treated for 6 and 24 hrs, respectively, indicating a very low cytotoxicity of the peptides.

Example 2

Effect of the Peptides on White Blood Cell (WBC) Mobilization

Figure 2:
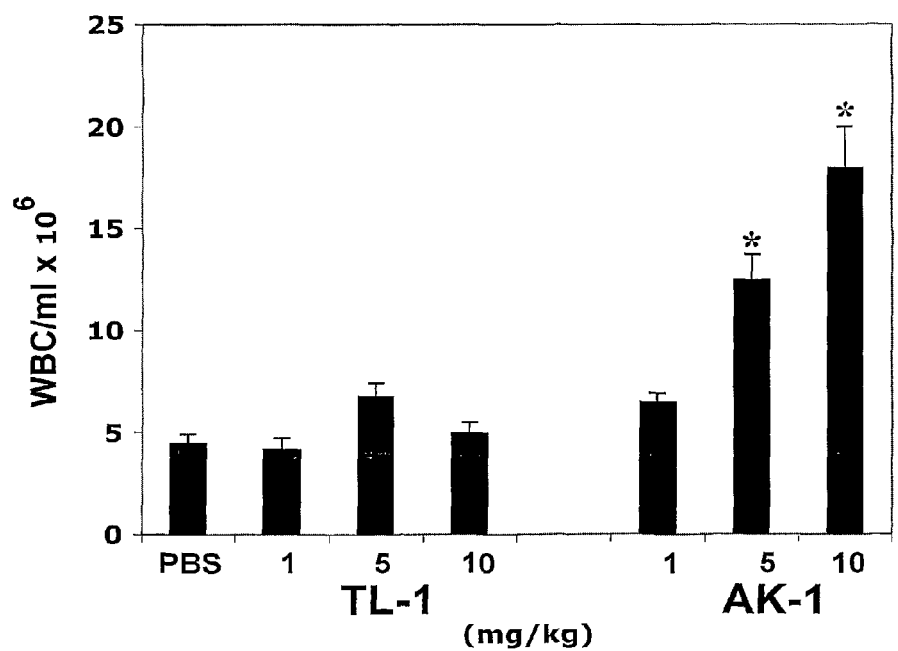
FIG. 2. Dose-response effect of TL-1 and AK-1 on mobilization of WBC. C57BL/6 mice were s.c. injected with 1, 5 or 10 mg/kg of TL-1 or AK-1. Control mice were injected with phosphate buffered saline (PBS). After 1-1.5 h, mice were sacrificed and WBC number in the PB was calculated. Data shown are the mean±SD of 3 separate experiments. *P<0.05 compared to control.

The cell mobilizing potential of the peptides was examined in intact C57BL/6 mice, using the protocol applied for AMD3100 (Broxmeyer, H. E., et al., 2005). First, the effect of different doses of the peptides was evaluated. Mice were s.c. injected with 1, 5 and 10 mg/kg of TL-1 (linear and cyclic) or AK-1, sacrificed 1-2 hr later and the total number of WBC in 1 ml of blood was determined (see Materials and Methods). It was found that linear TL-1 was ineffective at a dose of 1 mg/kg, but at doses of 5 and 10 mg/kg it induced WBC mobilization. AK-1 induced WBC mobilization in a clear dose-dependent manner (FIG. 2). In all tested doses, cyclic TL-1 did not induce WBC mobilization.

Figure 4:
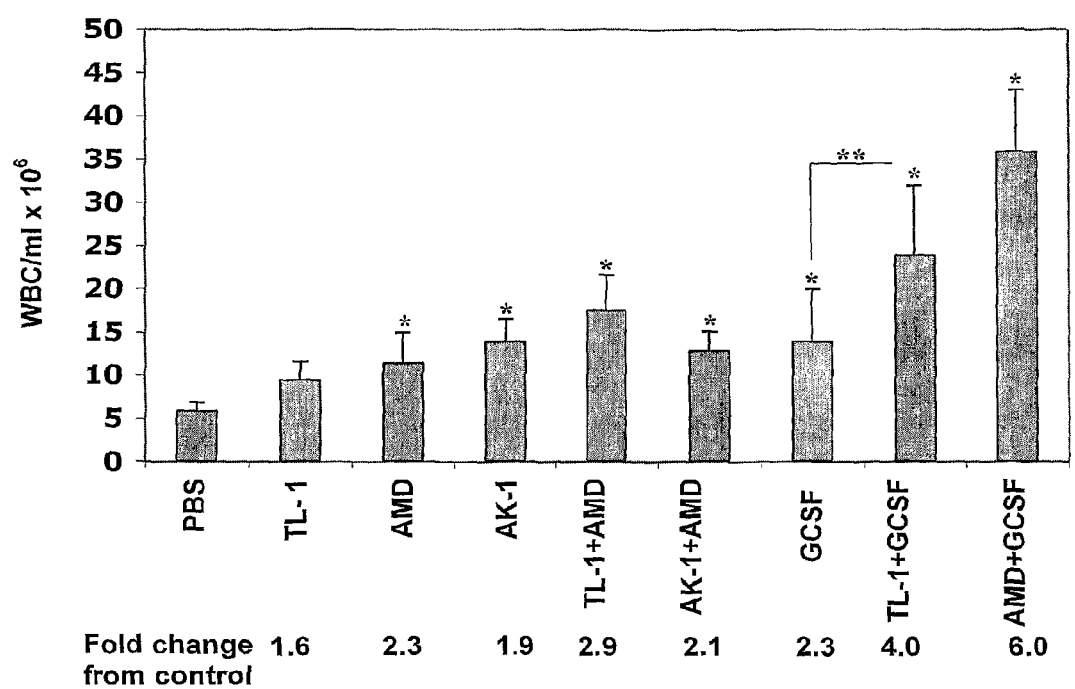
FIG. 4. TL-1 synergizes with G-CSF to mobilize WBC. C57BL/6 mice were s.c. injected with G-CSF 2.5 μg/twice a day for four days. Eighteen hrs after the last injection mice were s.c. injected with 5 mg/kg of either TL-1, AK-1 or AMD3100 (AMD), sacrificed 1.5 h later, and the number of WBC was calculated. Control mice were injected with PBS or with TL-1, AK-1 or AMD3100 without pre-treatment with G-CSF. Data shown are the mean±SD of 3 separate experiments. *P<0.05 compared to control. **Significant difference between two compared groups of mice.

Next, the mobilizing activity of the peptides in comparison with AMD3100 was examined, as well as their mobilizing activity in combination with AMD3100 or G-SCF. In these experiments, the peptides and AMD3100 were s.c. injected at a dose of 5 mg/kg and mice were sacrificed 1-2 hr later. G-SCF was injected s.c. at a concentration of 2.5 µg per mouse twice a day for 4 days; the peptides or AMD3100 were injected 18 hr after the last G-SCF injection and mice were sacrificed 1-2 hr later. Remarkably, the WBC mobilizing activity of AK-1 was found to be equal to that provided by AMD3100 (FIG. 4). The mobilizing capacity of TL-1 in the mouse model was weaker as compared to AMD3100 with no additive effect upon simultaneous injection of these two compounds. Similarly, the combination of AK-1 and AMD3100 also did not reveal an additive effect. Cyclic TL-1, injected with AMD3100, decreased its mobilizing capacity. The combination of TL-1 with G-SCF induced a significant additive effect as compared with separate injections of each compound. However, this additive effect was weaker than those obtained by combination of AMD3100 and G-CSF (FIG. 4).

Taken together, these findings show that (i) TL-1 and AK-1 induce WBC mobilization, with AK-1 demonstrating a stronger effect, and (ii) a combination of TL-1 and G-CSF provides a significant additive WBC mobilizing effect.

Example 3

Effect of the Peptides on Progenitor Cell Mobilization

Figure 3:
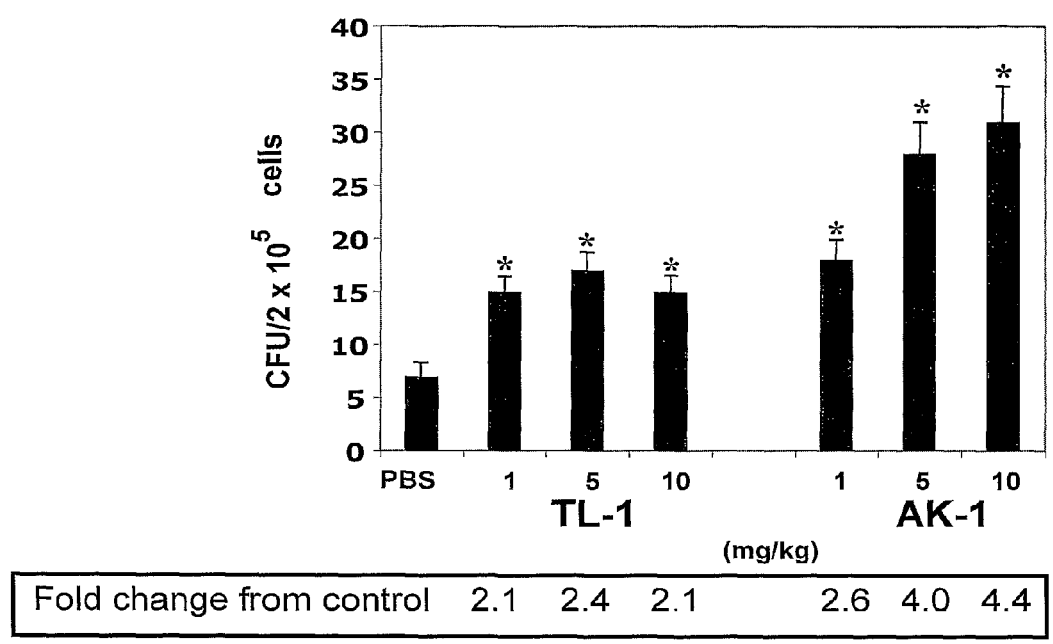
FIG. 3. Dose-response effect of TL-1 and AK-1 on mobilization of hematopoietic progenitor cells to peripheral blood. C57BL/6 mice were s.c. injected with 1, 5 or 10 mg/kg of TL-1 or AK-1. Control mice were injected with PBS. After 1-1.5 h, mice were sacrificed, peripheral blood mononuclear cells (PB MNC) were separated by Ficoll, seeded into the methylcellulose, and the number of colony-forming units (CFU) was estimated. Data shown are the number of CFU per 2×10$^5$ seeded PB MNC cells. Vertical bars represent standard deviation of duplicate experiments. *P<0.05 compared to control.
Figure 5:
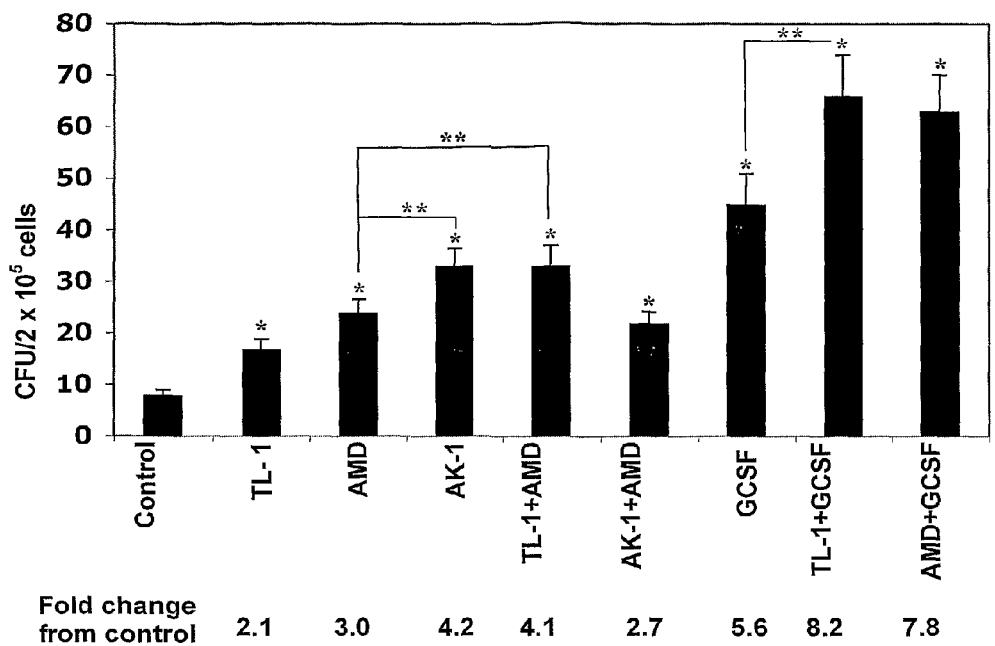
FIG. 5. TL-1 synergizes with G-CSF to mobilize hematopoietic progenitor cells to peripheral blood. C57BL/6 mice were s.c. injected with 5 mg/kg of AMD3100 (AMD), TL-1, AK-1, TL-1+AMD3100, or AK-1+AMD3100. Other mice were injected with G-CSF, alone or with TL-1 or AMD3100. Control mice were injected with PBS. After 1-1.5 h, mice were sacrificed, peripheral blood mononuclear cells (PB MNC) were separated by Ficoll, seeded into the methylcellulose, and the number of colony-forming units (CFU) was estimated. Data shown are the number of CFU per 2×10$^5$ seeded PB MNC cells. Vertical bars represent standard deviation of duplicate experiments. *P<0.05 compared to control.

In the same experiments, blood mononuclear cells were collected and tested for the presence of colony-forming cells reflecting the number of HPC. In the dose response experiments, linear TL-1 significantly induced mobilization of HPC, equally at all doses used, namely 1, 5 and 10 mg/kg. AK-1, at 1 mg/kg, induced HPC mobilization reaching the strongest effect at 5 and 10 mg/kg (FIG. 3). Cyclic TL-1 did not induce mobilization of HPC at doses of 1 and 5 mg/kg. At a dose of 10 mg/kg it revealed an inhibitory effect. As found for WBC mobilization, the capability of AK-1 to induce HPC mobilization in the mouse model was higher than that of TL-1. In addition, in an equal dose (5 mg/kg) the HPC mobilization capability of AK-1 was even stronger than that of AMD3100 (FIG. 5). In combination with AMD3100 or G-CSF, TL-1 revealed an additive effect. Cyclic TL-1 induced an inhibitory effect, and it also inhibited AMD3100-induced mobilization.

Altogether, these observations show that (i) Tl-1 and AK-1 induce strong mobilization of HPC, with AK-1 demonstrating a stronger effect, and (ii) a combination of TL-1 and G-CSF provides a significant additive HPC mobilizing effect.

Example 4

Effect of the Peptides on SDF-1 Secretion

Figure 6:
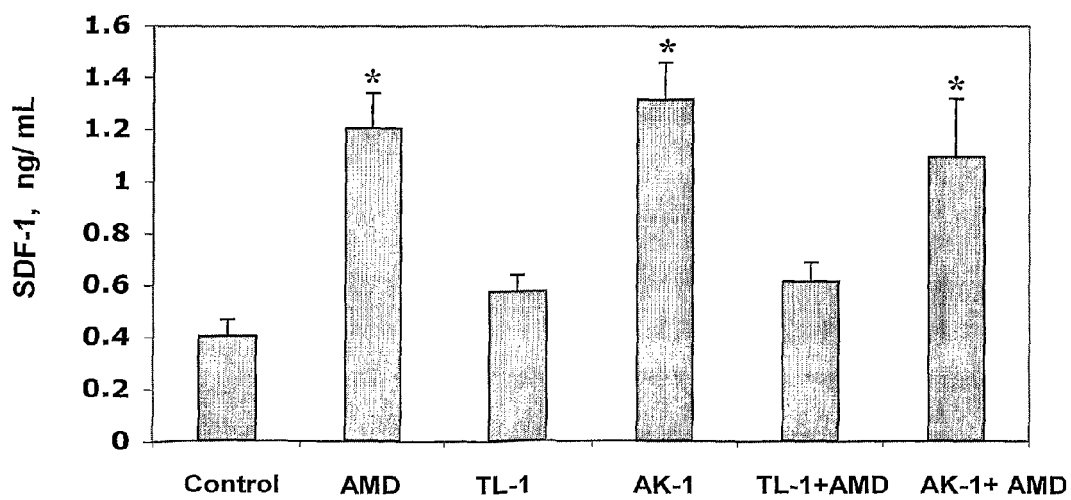
FIG. 6. AK-1 induces elevation of SDF-1 levels in murine plasma. C57BL/6 mice were s.c. injected with 5 mg/kg of AMD3100 (AMD), TL-1, AK-1, TL-1+AMD3100, or AK-1+AMD3100. Control mice were injected with PBS. After 1-1.5 h, mice were sacrificed, peripheral blood was collected, and the plasma levels of SDF-1 were detected by ELISA. Data shown are the mean±SD of 3 separate experiments. *P<0.05 compared to control.

As mentioned above, SDF-1/CXCR4 interactions are considered to play a major role in HSPC mobilization (Dar, A. et al., 2006). SDF-1 levels in plasma samples collected from mice injected with the peptides were examined. Administration of AMD3100 lead to a significant elevation in SDF-1 plasma levels as compared with mice injected with PBS (FIG. 6). Administration of AK-1 was also accompanied by a significant elevation in SDF-1 plasma levels (FIG. 6). However, administration of TL-1, as well as cyclic TL-1, did not induce increase in SDF-1 plasma levels in this model (FIG. 6).

Figure 7A:
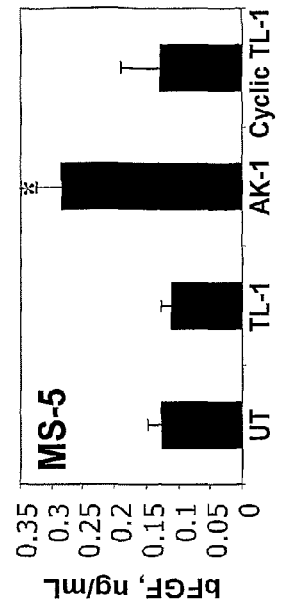
FIGS. 7A-7F. Effect of TL-1, AK-1 and cyclic TL-1 on SDF-1, bFGF and HGF secretion by different stromal cell lines. MS-5, MBA-15 and MG-63 cells were co-cultured with 10 μM TL-1, AK-1 or cyclic TL-1 in the serum free medium for 6 hrs, or without added peptide (UT). Levels of SDF-1 (A-C), bFGF (D) and HGF (E, F) were detected in the collected supernatants by ELISA. Data shown are the mean±SD of 2 separate experiments. *P<0.05 compared to control.
Figure 7B:
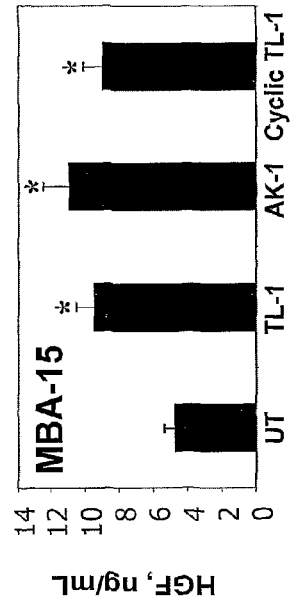
Figure 7C:
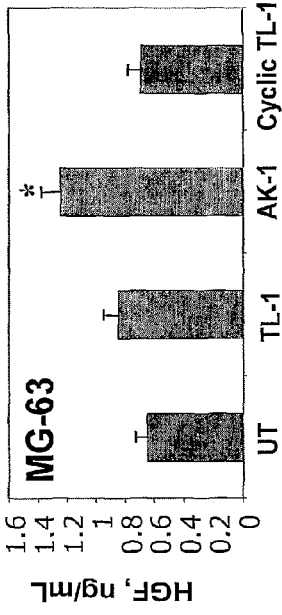

Because BM stromal cells, such as endosteal bone lining osteoblasts and endothelial cells are the main source of human and murine SDF-1, the capability of the peptides to affect SDF-1 secretion by mouse stromal MS-5 and MBA-15 cells, and human osteoblast MG-63 cells was examined. It was found that the levels of SDF-1 in the culture medium samples (supernatants) collected from all three studied cell lines preincubated for 3 hrs with TL-1 or AK-1 were significantly elevated as compared with untreated cells (FIG. 7A-C). Cyclic TL-1 also increased the levels of SDF-1 secretion by MS-5 and MBA-15 cells but much less as compared with TL-1 and AK-1, and in MG-63 cells it was ineffective. In these experiments, AMD3100 did not affect the levels of SDF-1 in the supernatants collected from all tested cells.

Figure 7D:
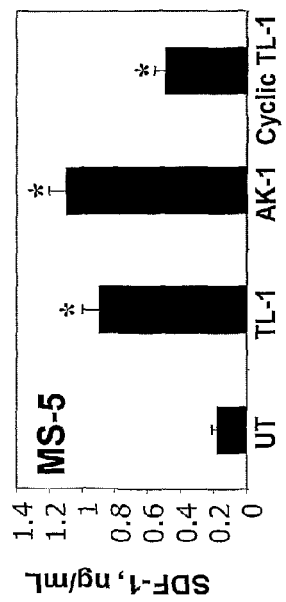
Figure 7E:
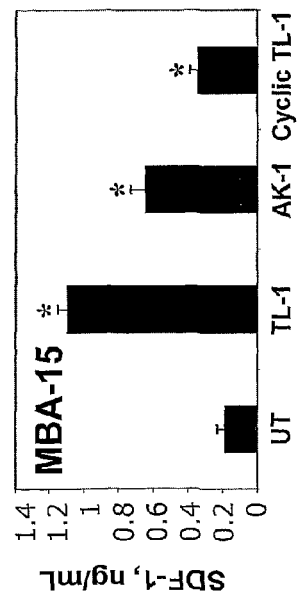
Figure 7F:
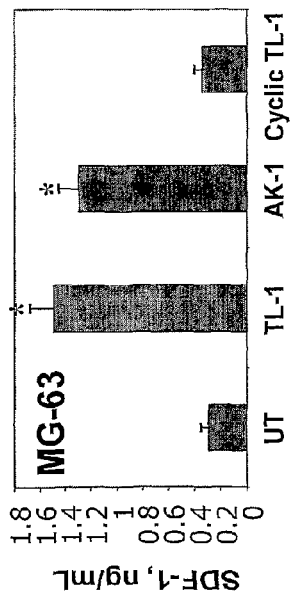

In order to examine the capability of the peptides to induce secretion of other proteins, the levels of Hepatocyte growth factor (HGF) and Basic fibroblast growth factor (bFGF) were detected in the same supernatants. Secretion of these two proteins into the supernatants collected from MBA-15 and MG-63 cells preincubated with AK-1 was found to be significantly elevated (FIG. 7D-F). TL-1 induced elevation of HGF in the supernatants collected from MBA-15 cells (FIG. 7E) and not from MG-63 cells (FIG. 7F) and also did not induce elevation of bFGF in MS-5 cell supernatants (FIG. 7C). Cyclic TL-1 induced elevation of HGF in the MBA-15 cell supernatants (FIG. 7D).

Example 5

Effect of the Peptides on Cell Migration In Vitro and In Vivo

Figure 9A:
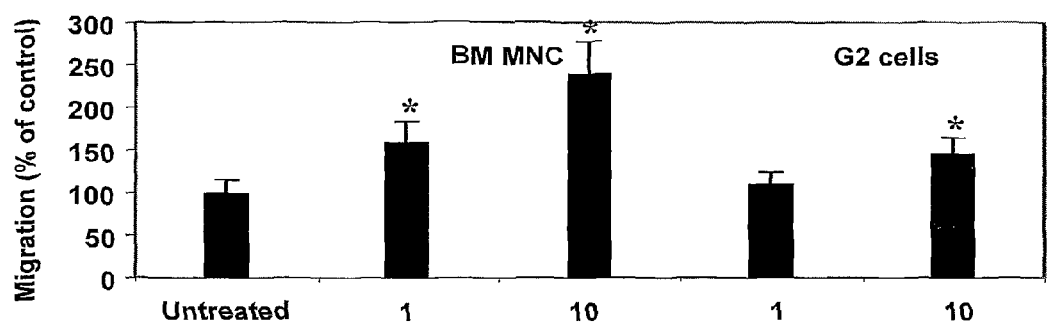
FIGS. 9A-9B. AK-1 increases SDF-1-induced migration and chemotaxis of G2 and mouse bone marrow mononuclear cells (BM MNC). (A) G2 cells and mouse BM MNC were preincubated with 1 and 10 μM AK-1 for 3 hrs in serum free medium, washed and allowed to migrate towards SDF-1. Migrated cells were collected and calculated by flow cytometry. Percentage of migrated cells is presented as compared to untreated control taken as 100%. (B) Untreated G2 cells and mouse BM MNC were put to the upper chambers of the transwell plates and allowed to migrate towards 1 and 10 μM AK-1 present the bottom chambers of the transwell plates for 4 hrs. Percentage of migrated cells is presented as compared to untreated (UT) control taken as 100%. Data shown are the mean±SD of 2 separate experiments. *P<0.05 compared to control.
Figure 9B:
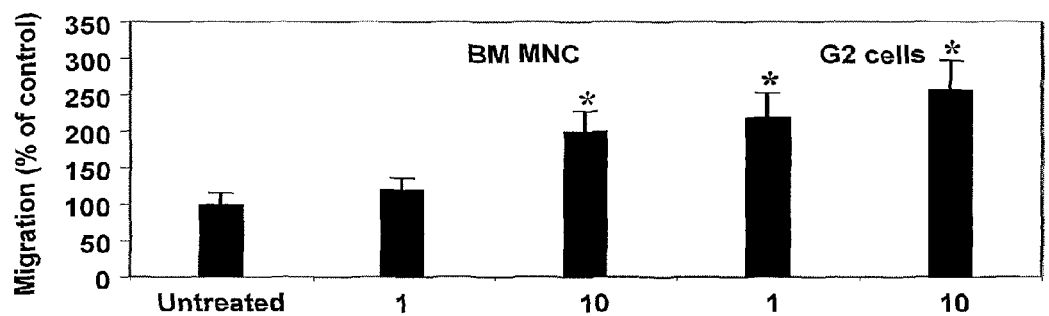

The apparent capability of the peptides to affect SDF-1 secretion in both in vivo and in vitro experiments suggests their potential influence on SDF-1-induced cell migration. To address this issue, the cells were incubated with the peptides for 3 hrs, washed and then allowed to migrate towards SDF-1. TL-1 at 10 µM significantly reduced such migration of various normal and malignant cell types (FIG. 8A); the strongest inhibitory effect was observed upon testing human cord blood $CD34^+$ cells where more than 90% inhibition of transwell migration was observed by applying TL-1 already at 1 µM. Significant inhibitory effect of TL-1 was observed already 10 min after preincubation that reached a peak after 3 hrs (FIG. 8B). An opposite (stimulating) effect was obtained when TL-1 was preincubated with human peripheral blood mononuclear cells (FIG. 8C) suggesting different effects of TL-1 on the migration of various human cell subpopulations. Cyclic TL-1 at 1 µM was ineffective, and at 10 µM it revealed a 2-fold inhibition of SDF-1-induced migration of G2 and U937 cells. AK-1 significantly up-regulated SDF-1-induced migration of G2 cells, primary human $CD3^+$ T as well as mouse BM mononuclear cells (FIG. 9). In the chemotaxis assay where different untreated cell migrated towards AK-1 present in the bottom chamber of the transwell plate, a very strong stimulating effect was demonstrated in a dose dependent manner (FIG. 9) whereas TL-1 and cyclic TL-1 were ineffective.

In the homing assay, pretreatment of G2 cells with TL-1 resulted in their elevated homing to the BM and spleen (Spl) of NOD/SCID mice whereas similar pretreatment with cyclic TL-1 resulted in decreased G2 cell homing to the spleen (FIG. 8D).

Example 6

Effect of the Peptides on CXCR4 Expression and MMP-2 Activity

Figure 10A:
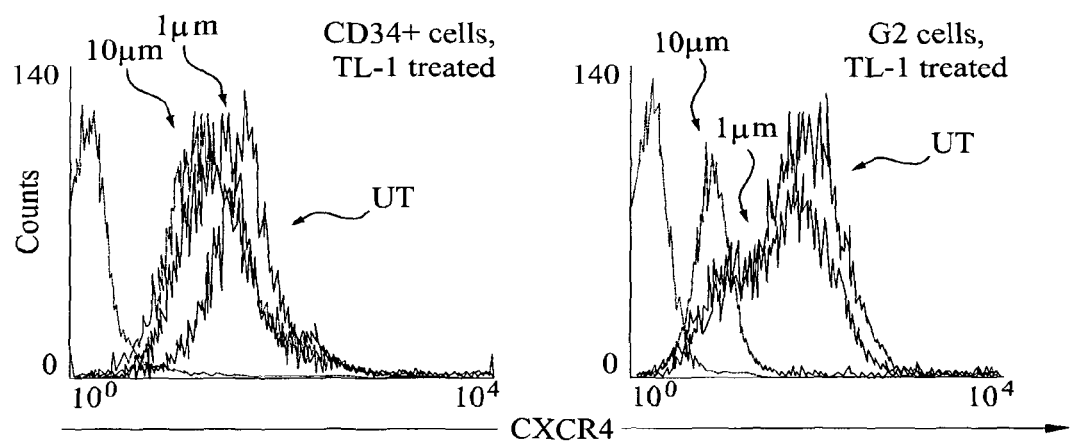
FIGS. 10A-10C. TL-1 and cTL1 down-regulate CXCR4 expression on human cord blood CD34$^+$ and G2 cells. Human cord blood CD34$^+$ and G2 cells were incubated with 1 or 10 μM TL-1 or cyclic TL-1 for 3 hrs or left untreated (UT), washed, stained with CXCR4 and CCR5 Ab and analyzed by flow cytometry. Representative histograms from 3 separate experiments are shown.
Figure 10B:
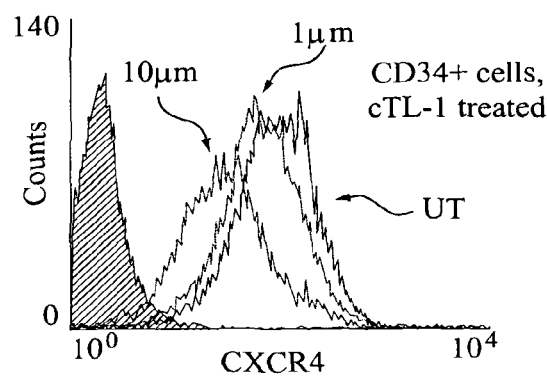
Figure 10C:
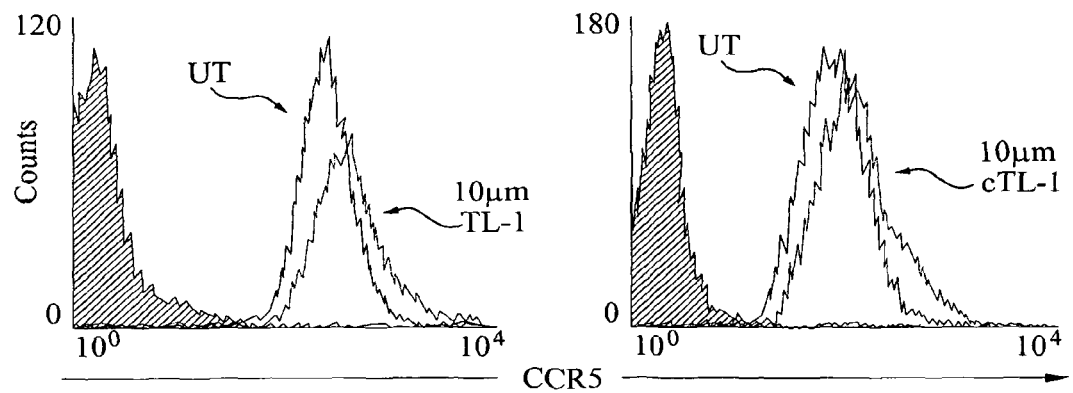

Recently, it has been shown that HBD3 could induce internalization of CXCR4 but not of CCR5 in the CEM T cells expressing both CXCR4 and CCR5 (Feng, Z. et al., 2006) implying CXCR4 specificity in HBD3 action. Herein it was found that preincubation of TL-1 with human cord blood $CD34^+$ and especially with G2 cells resulted in decreased CXCR4 expression (FIG. 10A) with no effect, however, in U937 and HL-60 cells. Cyclic TL-1 also decreased CXCR4 expression in $CD34^+$ (FIG. 10B) but not in G2 cells. Membrane expression of CCR5 (FIG. 10C) and CD45 was either unaffected or slightly increased on tested cells after preincubation with TL-1 and cyclic TL-1 suggesting that the capability of these peptides to decrease CXCR4 expression is cell type dependent.

Figure 11:
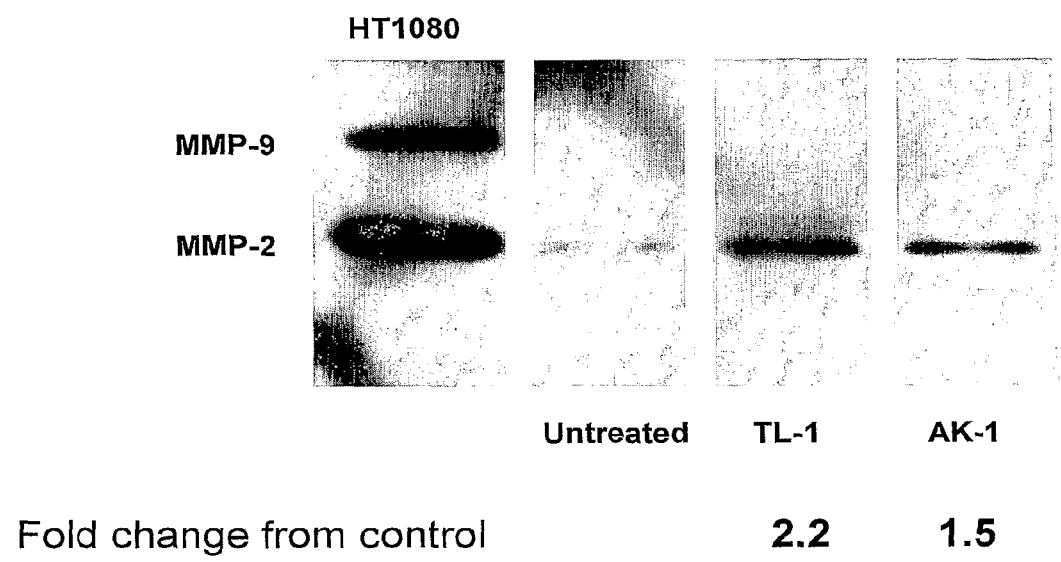
FIG. 11. TL-1 and AK-1 increase activity of MMP-2. MS-5 cells were co-cultured with 10 μM TL-1 or AK-1 in the serum free medium for 6 hrs. Activity of MMPs was examined by gelatin zymography. Supernatants collected from HT1080 cells served as a positive control. A representative gel from 2 separate experiments is shown.

Regarding MMPs, it was found herein that preincubation of MS-5 cells with TL-1 and AK-1 for 6 hrs resulted in increased (2.2- and 1.5-fold, respectively) MMP-2 activity in the supernatants (FIG. 11).

REFERENCES

Abraham, M., et al. (2007) Enhanced unique pattern of hematopoietic cell mobilization induced by the CXCR4 antagonist 4F-benzoyl-TN14003. Stem Cells 25, 2158-66.

Broxmeyer, H. E., et al. (2005) Rapid mobilization of murine and human hematopoietic stem and progenitor cells with AMD3100, a CXCR4 antagonist. J Exp Med 201, 1307-18.

Burger J A, Peled A. (2009) CXCR4 antagonists: targeting the microenvironment in leukemia and other cancers. Leukemia.; 23(1):43-52.

Dar, A., Kollet, O. & Lapidot, T. (2006) Mutual, reciprocal SDF-1/CXCR4 interactions between hematopoietic and bone marrow stromal cells regulate human stem cell migration and development in NOD/SCID chimeric mice. Exp Hematol 34, 967-75.

de Leeuw, E., Burks, S. R., Li, X., Kao, J. P. & Lu, W. (2007) Structure-dependent functional properties of human defensin 3. FEBS Lett 581, 515-20.

Devine S M, Vij R, Rettig M, Todt L, McGlauchlen K, Fisher N, Devine H, Link D C, Calandra G, Bridger G, Westervelt P, Dipersio J F (2008). Rapid mobilization of functional donor hematopoietic cells without G-CSF using AMD3100, an antagonist of the CXCR4/SDF-1 interaction. Blood. 112(4):990-8.

Dhople, V., Krukemeyer, A. & Ramamoorthy, A. (2006) The human beta-defensin-3, an antibacterial peptide with multiple biological functions. Biochim Biophys Acta 1758, 1499-512.

Feng, Z., Dubyak, G. R., Lederman, M. M. & Weinberg, A. (2006) Cutting edge: human beta defensin 3—a novel antagonist of the HIV-1 coreceptor CXCR4. J Immunol 177, 782-6.

Funderburg, N., et al. (2007) Human-defensin-3 activates professional antigen-presenting cells via Toll-like receptors 1 and 2. Proc Natl Acad Sci USA 104, 18631-5.

Gazitt, Y., Freytes, C. O., Akay, C., Badel, K. & Calandra, G. (2007) Improved mobilization of peripheral blood CD34+ cells and dendritic cells by AMD3100 plus granulocyte-colony-stimulating factor in non-Hodgkin's lymphoma patients. Stem Cells Dev 16, 657-66.

Goichberg, P., et al. (2006) cAMP-induced PKCzeta activation increases functional CXCR4 expression on human CD34+ hematopoietic progenitors. Blood 107, 870-9.

Hendrix, C. W., et al. (2004) Safety, pharmacokinetics, and antiviral activity of AMD3100, a selective CXCR4 receptor inhibitor, in HIV-1 infection. J Acquir Immune Defic Syndr 37, 1253-62.

Hinrichsen, K., et al. (2008) Mouse beta-defensin-14, an antimicrobial ortholog of human beta-defensin-3. Antimicrob Agents Chemother 52, 1876-9.

Hoover D M, Wu Z, Tucker K, Lu W, Lubkowski J. (2003). Antimicrobial characterization of human beta-defensin 3 derivatives. Antimicrob Agents Chemother. 47(9):2804-9.

Kalinkovich, A., et al. (2006) Functional CXCR4-expressing microparticles and SDF-1 correlate with circulating acute myelogenous leukemia cells. Cancer Res 66, 11013-20.

Klüver E, Schulz-Maronde S, Scheid S, Meyer B, Forssmann W G, Adermann K. (2005). Structure-activity relation of human beta-defensin 3: influence of disulfide bonds and cysteine substitution on antimicrobial activity and cytotoxicity. Biochemistry. 44(28):9804-16.

Krishnakumari V, Singh S, Nagaraj R. (2006). Antibacterial activities of synthetic peptides corresponding to the carboxy-terminal region of human beta-defensins 1-3. Peptides. 27(11):2607-13.

Lapidot, T. & Petit, I. (2002) Current understanding of stem cell mobilization: the roles of chemokines, proteolytic enzymes, adhesion molecules, cytokines, and stromal cells. Exp Hematol 30, 973-81.

Liles, W. C., et al. (2005) Augmented mobilization and collection of CD34+ hematopoietic cells from normal human volunteers stimulated with granulocyte-colony-stimulating factor by single-dose administration of AMD3100, a CXCR4 antagonist. Transfusion 45, 295-300.

Nishimura, M., et al. (2004) Effect of defensin peptides on eukaryotic cells: primary epithelial cells, fibroblasts and squamous cell carcinoma cell lines. J Dermatol Sci 36, 87-95.

Niyonsaba, F., Ushio, H., Nagaoka, I., Okumura, K. & Ogawa, H. (2005) The human beta-defensins (-1, -2, -3, -4) and cathelicidin LL-37 induce IL-18 secretion through p38 and ERK MAPK activation in primary human keratinocytes. J Immunol 175, 1776-84.

Rohrl, J., Yang, D., Oppenheim, J. J. & Hehlgans, T. (2008) Identification and Biological Characterization of Mouse beta-defensin 14, the orthologue of human beta-defensin 3. J Biol Chem 283, 5414-9.

Schneider, J. J., Unholzer, A., Schaller, M., Schafer-Korting, M. & Korting, H. C. (2005) Human defensins. J Mol Med 83, 587-95.

Soruri, A., Grigat, J., Forssmann, U., Riggert, J. & Zwirner, J. (2007) beta-Defensins chemoattract macrophages and mast cells but not lymphocytes and dendritic cells: CCR6 is not involved. Eur J Immunol 37, 2474-86.

Spiegel, A., et al. (2004) Unique SDF-1-induced activation of human precursor-B ALL cells as a result of altered CXCR4 expression and signaling. Blood 103, 2900-7.

Tamamura, H., et al. (2005) Structure-activity relationship studies on CXCR4 antagonists having cyclic pentapeptide scaffolds. Org Biomol Chem 3, 4392-4.

Tavor S, Petit I, Porozov S, Avigdor A, Dar A, Leider-Trejo L, Shemtov N, Deutsch V, Naparstek E, Nagler A, Lapidot T. (2004) CXCR4 regulates migration and development of human acute myelogenous leukemia stem cells in transplanted NOD/SCID mice. Cancer Res. 64(8):2817-24.

Tigue, C. C., et al. (2007) Granulocyte-colony stimulating factor administration to healthy individuals and persons with chronic neutropenia or cancer: an overview of safety considerations from the Research on Adverse Drug Events and Reports project. Bone Marrow Transplant 40, 185-92.

Varoga, D., et al. (2005) Human beta-defensin 3 mediates tissue remodeling processes in articular cartilage by increasing levels of metalloproteinases and reducing levels of their endogenous inhibitors. Arthritis Rheum 52, 1736-45.

Wu, Z., et al. (2003) Engineering disulfide bridges to dissect antimicrobial and chemotactic activities of human beta-defensin 3. Proc Natl Acad Sci USA 100, 8880-5.

Zeng Z, Shi Y X, Samudio L I, Wang R Y, Ling X, Frolova O, Levis M, Rubin J B, Negrin R R, Estey E H, Konoplev S, Andreeff M, Konopleva M (2008). Targeting the leukemia microenvironment by CXCR4 inhibition overcomes resistance to kinase inhibitors and chemotherapy in AML. Blood (Epub).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A cyclized peptide having the sequence of 1,10-cyclo[RGRKCCRRKK], (cTL-1, SEQ ID NO: 3), wherein the arginine at position 1 is linked through a peptide bond to the lysine at position 10.

2. A pharmaceutical composition containing an effective amount of the peptide of claim 1, and one or more pharmaceutically accepted carriers, excipients or diluents.

3. A method for reducing or inhibiting cancer metastasis in a subject in need thereof, comprising administering to the subject an effective amount of a peptide as set forth in claim 1.

4. The method of claim 3, wherein the subject is afflicted with a tumor characterized by CXCR4 expression of at least a portion of the tumor cells.

5. The method of claim 4, wherein the tumor is of hematopoietic origin.

6. The method of claim 4, wherein the tumor is leukemia.

7. The peptide of claim 1 being up to 16 amino acids in length.

8. A method for reducing or inhibiting cancer metastasis in a subject in need thereof, comprising administering to the subject an effective amount of a peptide as set forth in claim 7.

* * * * *

```
SEQUENCE LISTING

<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: synthetic peptide derived from human beta
      defensin 3

<400> SEQUENCE: 1

Arg Gly Arg Lys Cys Cys Arg Arg Lys Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic peptide derived from mouse beta
      defensin 14

<400> SEQUENCE: 2

Ser Gly Arg Lys Cys Cys Arg Lys Lys Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic cyclized peptide
<220> FEATURE:
<221> NAME/KEY: MISC_FEATURE
<222> LOCATION: (1)..(10)
<223> OTHER INFORMATION: cyclic peptide (1, 10-cyclo-)
<220> FEATURE:
<221> NAME/KEY: MISC_FEATURE
<222> LOCATION: (1)..(10)
<223> OTHER INFORMATION: peptide bond

<400> SEQUENCE: 3

Arg Gly Arg Lys Cys Cys Arg Arg Lys Lys
1               5                   10
```